US011222648B1

United States Patent
Hansen et al.

(10) Patent No.: US 11,222,648 B1
(45) Date of Patent: Jan. 11, 2022

(54) POSITIVE PRESSURE VENTILATION MICROPHONE SYSTEM, NEBULIZER, AND RELATED METHODS

(71) Applicant: ReddyPort Inc., Salt Lake City, UT (US)

(72) Inventors: Andrew S Hansen, Bountiful, UT (US); Rian J. Wendling, Salt Lake City, UT (US); Richard A. Kreifeldt, South Jordan, UT (US)

(*) Notice: Subject to any disclaimer, the term of this patent is extended or adjusted under 35 U.S.C. 154(b) by 0 days.

(21) Appl. No.: 16/872,337

(22) Filed: May 11, 2020

Related U.S. Application Data

(60) Provisional application No. 62/846,662, filed on May 11, 2019, provisional application No. 62/847,317, filed on May 13, 2019.

(51) Int. Cl.
| | | |
|---|---|---|
| *G10L 21/0316* | (2013.01) | |
| *A61M 16/06* | (2006.01) | |
| *H04R 1/02* | (2006.01) | |
| *H04R 1/08* | (2006.01) | |
| *A61M 11/00* | (2006.01) | |

(52) U.S. Cl.
CPC ......... *G10L 21/0316* (2013.01); *A61M 16/06* (2013.01); *H04R 1/02* (2013.01); *H04R 1/08* (2013.01); *A61M 11/005* (2013.01); *A61M 2205/502* (2013.01); *A61M 2205/8206* (2013.01)

(58) Field of Classification Search
CPC ......... G10L 21/0316; H04R 1/02; H04R 1/08; A61M 16/06; A61M 11/005; A61M 2205/8206; A61M 2205/502; A62B 18/08
See application file for complete search history.

(56) References Cited

U.S. PATENT DOCUMENTS

| | | | |
|---|---|---|---|
| 2,123,196 A | 7/1938 | Millard | |
| 4,506,759 A * | 3/1985 | Fatovic | H04R 1/288 |
| | | | 181/151 |
| 4,901,356 A * | 2/1990 | Bauer | A62B 18/08 |
| | | | 381/344 |
| 5,224,474 A | 7/1993 | Bloomfield | |
| 6,430,298 B1 | 8/2002 | Kettl | |
| 6,811,538 B2 | 11/2004 | Westbrook | |
| 9,364,632 B2 | 6/2016 | Haibach | |

(Continued)

FOREIGN PATENT DOCUMENTS

| | | |
|---|---|---|
| WO | WO2017/048485 | 3/2017 |
| WO | WO2018/200535 | 11/2018 |

OTHER PUBLICATIONS

Khaled F. El-Said, "Assessment of Ambeient Noise Levels in The Intesnsive Care Unit of a University Hospital" J Family community Med. May-Aug. 2009; 16(2): 53-57.

(Continued)

*Primary Examiner* — Kendra D Carter
*Assistant Examiner* — Arielle Wolff
(74) *Attorney, Agent, or Firm* — Alpine IP

(57) ABSTRACT

A non-invasive ventilation voice amplification system includes a microphone module for placement in a non-invasive ventilation mask. The microphone module has a microphone element for detecting a patient's voice and a speaker for projecting the voice. The microphone module connects to a controller module that houses electronics for processing and amplifying the audio signal.

20 Claims, 15 Drawing Sheets

(56) References Cited

U.S. PATENT DOCUMENTS

| | | | |
|---|---|---|---|
| 10,136,225 B2 | 11/2018 | Register | |
| 10,681,469 B2 | 6/2020 | Register | |
| 2007/0157931 A1* | 7/2007 | Parker | A61M 11/005 128/204.23 |
| 2009/0308384 A1* | 12/2009 | Power | A61M 16/08 128/200.14 |
| 2010/0319691 A1 | 12/2010 | Lurie et al. | |
| 2012/0285465 A1 | 11/2012 | Pierro | |
| 2013/0265702 A1* | 10/2013 | Merenda | G06F 1/105 361/679.01 |
| 2014/0081631 A1 | 3/2014 | Zhu et al. | |
| 2014/0109899 A1* | 4/2014 | Boucher | A61M 16/14 128/200.18 |
| 2014/0216448 A1* | 8/2014 | Kihlberg | H03G 3/32 128/201.19 |
| 2014/0338672 A1 | 11/2014 | D'Souza | |
| 2015/0246200 A1 | 9/2015 | Neff, Jr. | |
| 2016/0001110 A1 | 1/2016 | Hamilton | |
| 2016/0101301 A1 | 4/2016 | Kihlberg | |
| 2017/0368383 A1* | 12/2017 | Riccio | A61M 16/0875 |
| 2018/0133429 A1* | 5/2018 | Reddy | A61M 16/20 |

OTHER PUBLICATIONS

Thomas Koch, "Design of Micropower Microphone and Speech Detection Circuits" Master's Thesis at the Institute of Neuroinformatics, Zurich, Apr. 29, 2008.

Pieter Roel Tuinman, "A New Speech Enhancement Device for Critically Ill Patients With Communication Problems: A Prospective Feasibility Study." Intensive Care Med (2017) 43:460-462, Nov. 21, 2016.

Jean A. Sulivan, "Development of Hearing in Noise Test (HINT) for the Measurement of Speech Reception Thresholds in in Quiet and in Noise," Journal of Acoustical Society of America, Oct. 25, 2993.

Samuel D. Chua, "Speech Enhancement During BiPAP Use for Persons Living With ALS," Thesis submitted to University of British Columbia, Nov. 2012.

Rockwell Collins, "Sweep-On Fullface crew oxygen mask system > data sheet," Lenexa KS, Oct. 2018.

J. Lewis, "Understanding Microphone Sensitivity" Analog Dialogue 46-5 Back Burner (May 2012) (www.analog.com/analogdialogue).

* cited by examiner

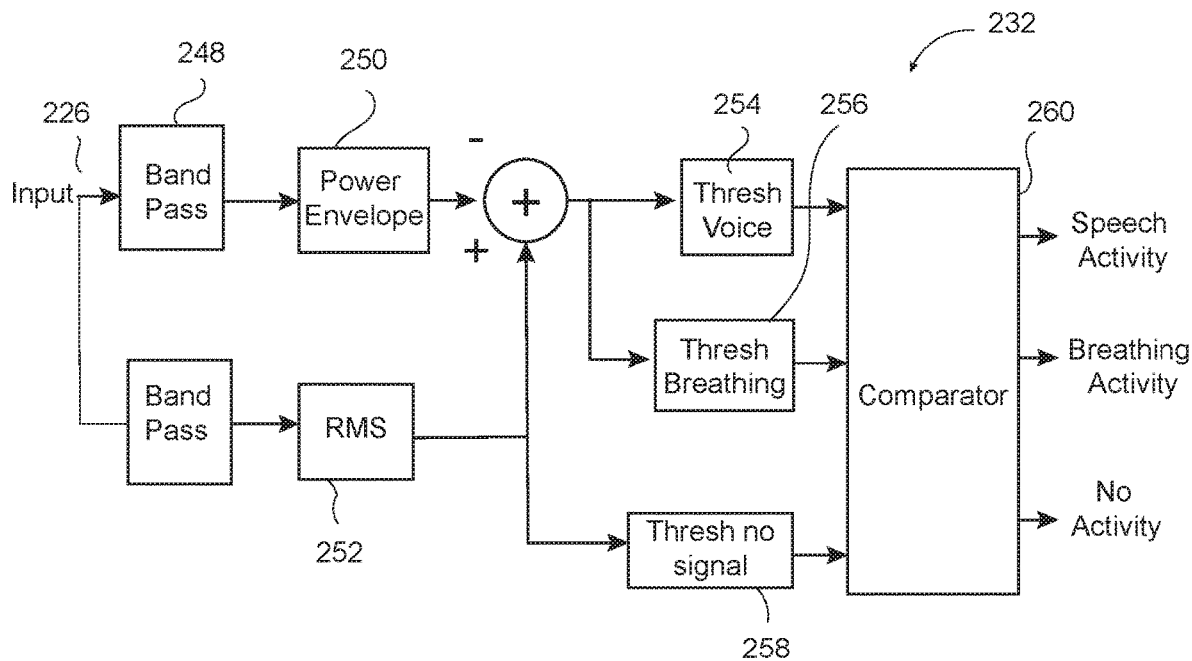
*Fig. 8A*
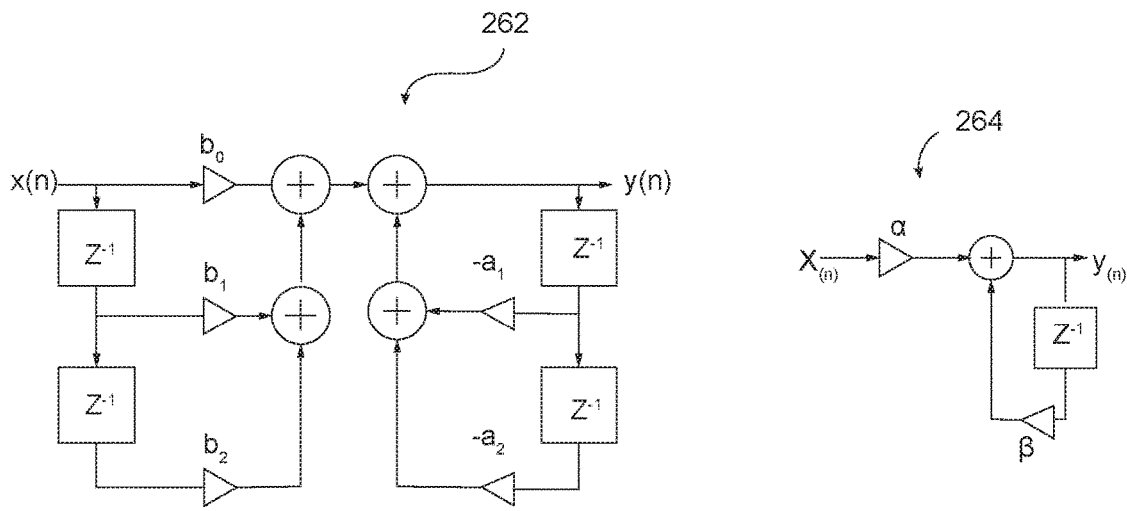 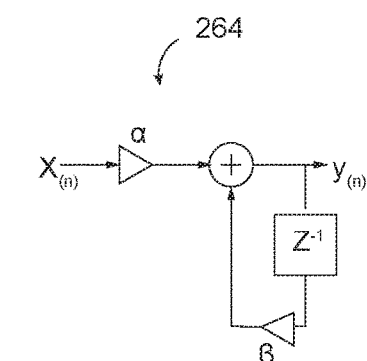
*Fig. 8B*          *Fig. 8C*

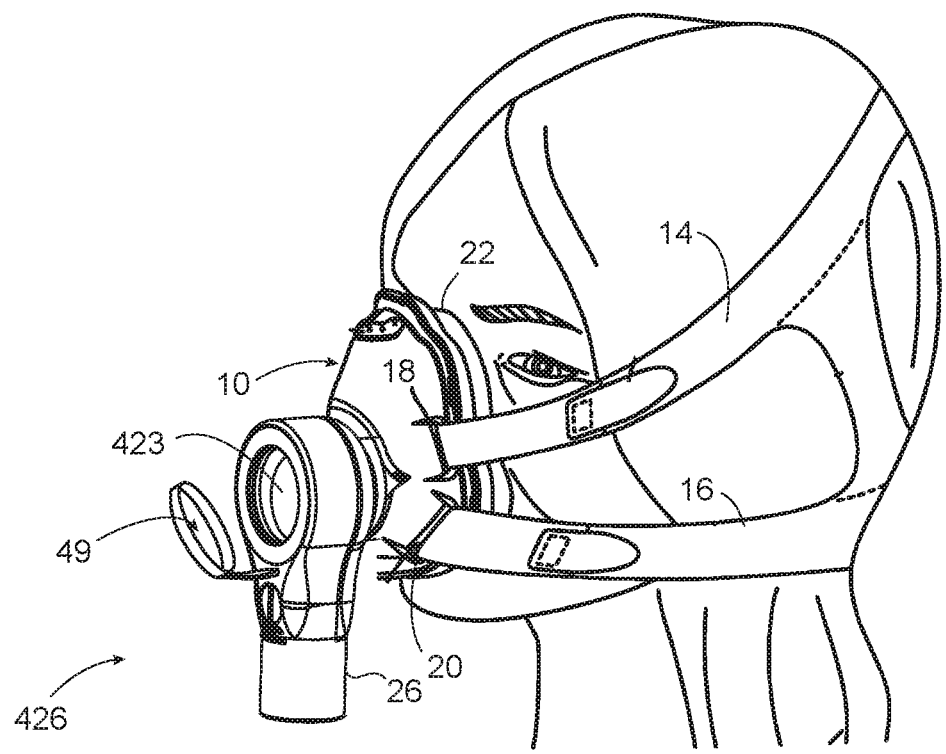
Fig. 13A
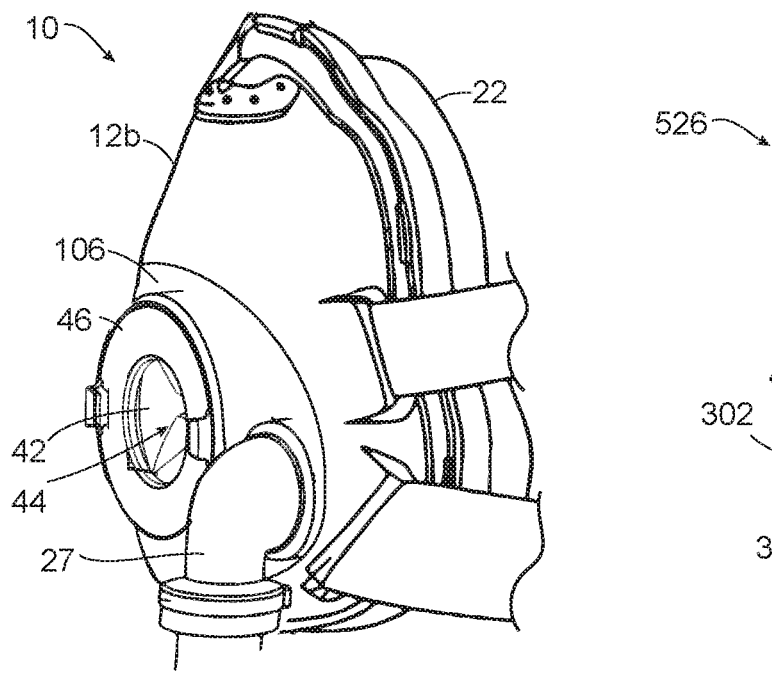
Fig. 13B
Fig. 14

POSITIVE PRESSURE VENTILATION MICROPHONE SYSTEM, NEBULIZER, AND RELATED METHODS

CROSS-REFERENCE TO RELATED APPLICATIONS

This application claims the benefit of U.S. Provisional Application Ser. No. 62/846,662, filed May 11, 2019 and titled "Positive Pressure Ventilation Microphone System, Nebulizer, and Related Methods," and 62/847,317, filed May 13, 2019, titled "Positive Pressure Ventilation Elbow Connectors, Appliance Modules, and Related Methods and Systems." The foregoing applications are hereby incorporated herein by reference in their entirety.

BACKGROUND

1. Field of the Invention

The present invention relates to devices and method for providing voice amplification and nebulization through a non-invasive positive pressure ventilation mask.

2. Related Technology

Positive pressure ventilation (PPV) masks are currently used in the medical field for patients with poor oxygen saturation, sleep apnea, and other related respiratory problems. The mask includes a peripheral flexible membrane that contacts the face of the patient and creates a seal with the face using the positive pressure. An example of a positive pressure ventilation mask is disclosed in U.S. Pat. No. 6,513,526 to Kwok. These types of masks used with a ventilator can provide positive pressure airflow, for critically ill patients can do so without the need to intubate the patient or allow earlier extubation.

Positive pressure masks require an effective seal around the facial area and can be a hassle for clinicians or users to properly place. Once in place, the positive pressure in the mask assists the patient's breathing by providing a proper amount of forced air necessary to maintain adequate breathing and exhalation. In a matter of hours or days, the mask can cause discomfort to the patient from dry mouth or nose, nasal congestion, rhinitis or runny nose, facial irritations, bloody noses, dry mucosal tissue, dry lips, increased risk of respiratory infection, or other difficulties managing oral or nasal airway.

Positive pressure masks are also used to treat sleep apnea. While these patients are typically not critically ill, they suffer from the inconvenience of dryness of the airway and the inability to access their oral airway without taking the mask off.

SUMMARY

The present invention relates to positive pressure ventilation microphone systems and nebulizers. The microphone devices and systems include a microphone module having a housing that defines an adapter configured to be inserted through a port of a positive pressure ventilation mask and form a seal so as to maintain therapeutic pressure in the mask. The microphone module includes a microphone element positioned on an inside portion of the module and a loudspeaker positioned on an outside portion. With the module inserted into the port of the mask, the microphone element is positioned in the mask and detects the speech of the patient. The loudspeaker is positioned outside the mask and projects the patient's speech. The microphone system includes a controller module that is electrically coupled to the microphone module and receives and processes the audio from the microphone element and then outputs the speech to the loudspeaker. The controller module can be mounted to a ventilator, IV pole, or bedrail in a patient room and connected to the patient microphone module through a wired connection.

In yet another embodiment of the invention, the system can include a nebulizer module. The nebulizer module can have a housing that forms an adapter configured to be inserted through a port of a positive pressure ventilation mask and form a seal with the port to maintain therapeutic pressure in the mask. The nebulizer includes an aerosol generator in fluid communication with a reservoir and is configured to deliver nebulized liquid into the mask. The nebulizer includes a housing with a wire connector for electrically coupling the nebulizer to a controller module. The controller module includes electronics for driving the mesh nebulizer and a user interface for allowing the nebulizer to be operated. In some embodiments, the electronics for operating the microphone module and the electronics for operating the nebulizer may be housed within the same housing of the controller module and/or on the same circuit board.

DESCRIPTION OF DRAWINGS

FIG. 8A is a circuit diagram of signal analyzer module for processing of FIG. 7;

FIG. 8B is a circuit diagram of the bandpass filter of FIG. 8A;

FIG. 8C is an RC low pass filter of FIG. 8A to adjust timing;

FIG. 13A illustrates an alternative embodiment of a full face positive pressure mask with an access port;

FIG. 13B illustrates yet another embodiment of a full face positive pressure mask with an access port;

FIG. 14 illustrates an alternative embodiment of an elbow with a swivel connector.

DETAILED DESCRIPTION

The positive pressure ventilation (PPV) microphone systems and modules of the present invention utilize a positive pressure ventilation mask, preferably one with an access port. The access port may be an opening with a removable cap or a valve that can be selectively opened to attach the microphone module. The access port may be built into the shell (also referred to as the mask body) of a PPV mask or into a connector (e.g., elbow) of the PPV mask. The valve may be a slit valve or a valve that seals under the pressure of the ventilator (also referred to herein as a self-sealing valve). The valve may also be self-reverting (i.e., made of a material and having a configuration that will revert back to its original configuration when inverted by an object being pulled through the valve).

Figure 1A:
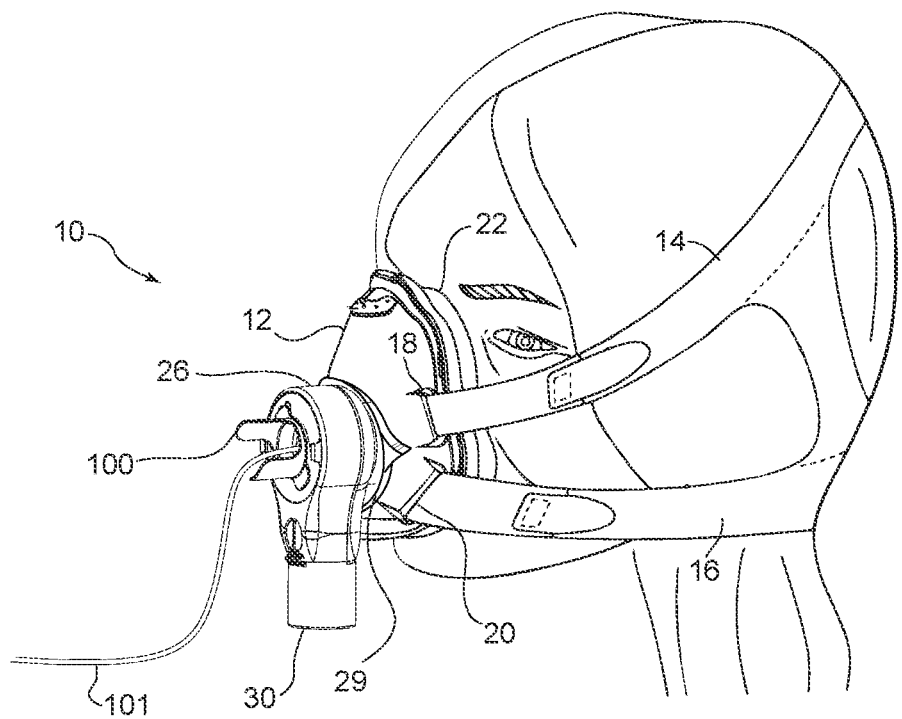
FIG. 1A illustrates a full-face positive pressure mask, including an elbow connector with a microphone module.
Figure 1B:
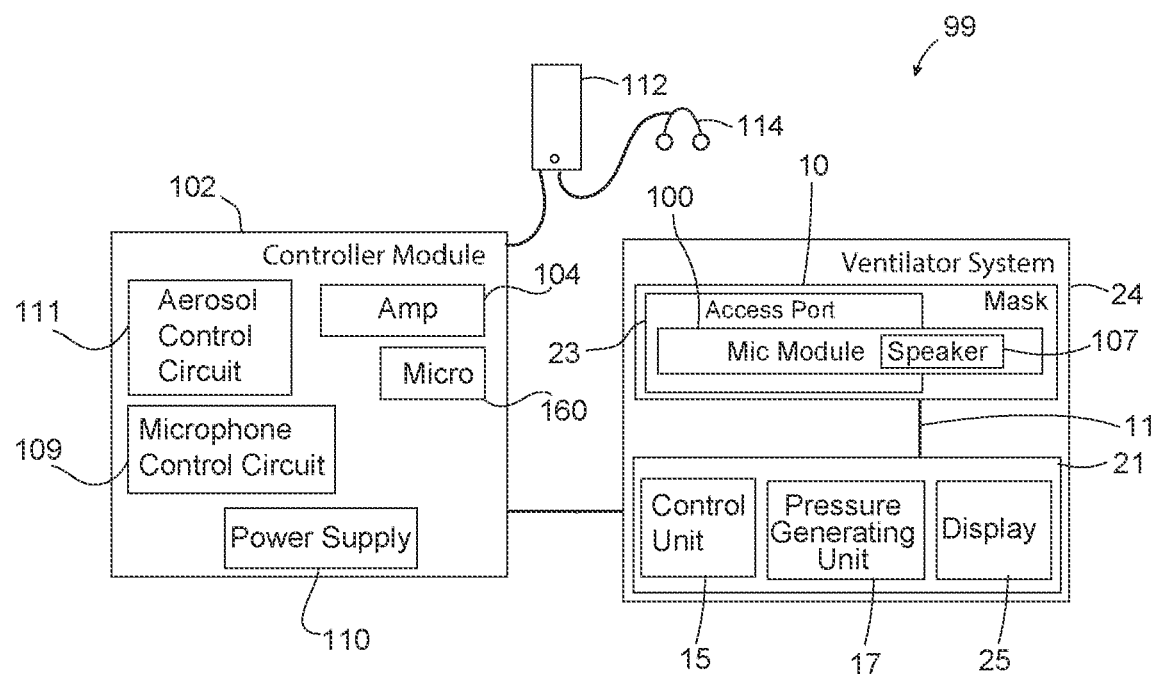
FIG. 1B is a block diagram of a positive pressure ventilator microphone system that includes the mask and microphone module of FIG. 1A.

FIGS. 1A and 1B illustrate a positive pressure ventilation (PPV) mask 10 and a voice amplification system 99. The mask 10 includes a mask body 12 (also referred to herein as a "shell"). As shown in FIG. 1B, ventilator system 24 includes the mask 10, access port 23, and a microphone module 100, which includes a housing that defines an adapter configured to form a positive pressure ventilation seal with access port 23. Microphone module 100 is removably connected to access port 23 and can be removed such that a nebulizer module 350 (FIG. 5) can be inserted and electrically coupled to controller module 102.

Figure 1C:
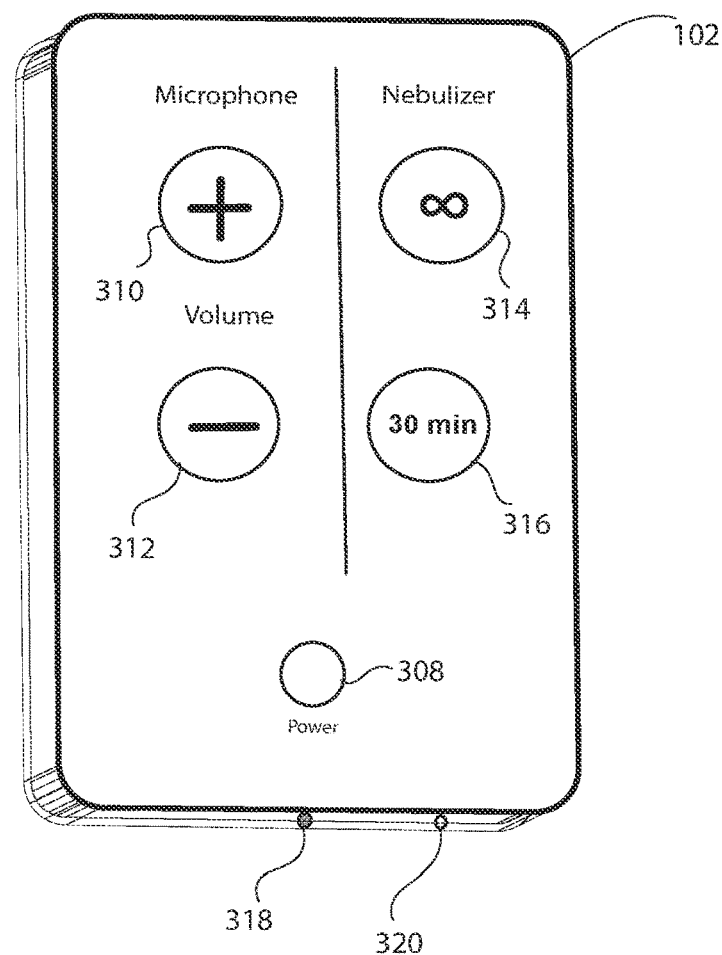
FIG. 1C is a perspective view of the controller module of the system of FIG. 1B.
Figure 1D:
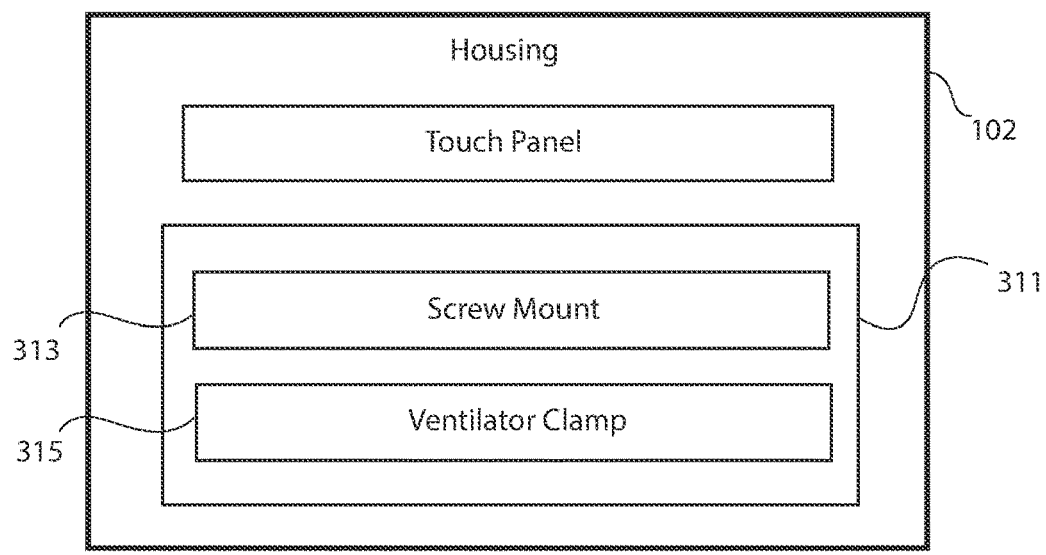
FIG. 1D is a block diagram of an attachment mechanism of the controller module of FIG. 1C.

FIG. 1C illustrates a controller module 102 with touch panel for receiving user provided input. Controller module 102, includes volume up button 310 and volume down button 312 for adjusting the volume of the speaker in the microphone module. Control module 102 also includes first nebulizer button 314 that upon being selected causes the aerosol control circuit to power a vibrating mesh nebulizer continuously. Selecting button 316 causes the aerosol control circuit to power the nebulizer for a set period of time (e.g., 30 minutes). Power button 308 allows the device to be turned on and off. Controller module 102 can also have any number of LEDs of one or more colors that indicate a status of the microphone or nebulizer or indicate that power is on. The buttons 310, 312, 314, and 316 can be backlit and/or have lighting that indicates if the microphone or conversely the nebulizer is in operation. Controller module 102 may also include a connector 318. Connector 318 can include a bayonet lock or other suitable lock for connecting a cable. In some embodiments connector 318 is at least 4, 5, 6, 7, 8, or 9 pins and receives a low level microphone signal and outputs a amplified voice signal or a aerosol generator signal to power the nebulizer. Connector 320 may be an auxiliary out and used to connect a third party device (e.g., a cell phone) to the controller and transmit the patient's voice to another person such as a loved one.

Ventilator system 24 also includes a ventilator unit 21 that connects to inlet 30 (FIG. 1A) of the elbow 26 via a flexible hose (FIG. 4) to form a ventilator circuit 11. Ventilator unit 21 includes a pressure sensor that senses pressure in the system and the sensed pressure is used by ventilator control unit 15 to control pressure by driving a pressure generating unit 17 (e.g., an impeller). Parameters of the ventilator can be displayed on display 25 and input received through a user interface (not shown). Ventilators used with the PPV masks of the invention are continuous pressure ventilators and preferably bi-level ventilation which is typically important for critical care patients.

Mask 10 is configured to be fluidly coupled to ventilator 21 through an air supply connector such as elbow 26 and secured to the head of the patient. Mask body 12 can be secured using straps (e.g., upper strap 14 and lower strap 16) or any other suitable securement mechanism suitable for attachment to the head. Straps 14 and 16 connect to eyelets 18 and 20, respectively, on mask body. Straps 14 and 16 connect to eyelets on corresponding locations (not shown) on an opposite side of body 12. The straps secure the mask to the head, which allows a positive pressure seal to be obtained and also avoids movement of the mask relative to the head that could cause air leaks that diminish the positive air treatment.

At the periphery of the mask body 12, mask 10 includes a cushion 22 that includes a flexible membrane (i.e., a flap) that can form a seal with the face of the patient when positive pressure is delivered from pressure generating unit 17 through elbow 26 and into an opening in mask body 12. Cushion 22 forms a seal with the patient's face in a nasal bridge region, a cheek region and a lower lip/chin region of the patient's face. The cushion may be constructed of one or more relatively soft, elastomeric materials connected to the mask body, which is typically constructed of a second material (or the same material but thicker) that is more rigid than the cushion. The cavity of mask body 12 forms a positive air pressure chamber between it and the face of a person. For purposes of this invention the term "within the mask" means the chamber defined by the mask when on the face of a person.

Masks having membranes suitable for sealing around the mouth and nose of a patient using positive pressure are described in U.S. Pat. No. 9,119,931 to D'Souza, U.S. Pat. No. 9,295,799 to McAuley; U.S. Pat. No. 6,513,526 to Kwok, and U.S. Pat. No. D464,728 to Paul, and international application publication WO2017021836A1 to Rose, all of which are hereby incorporated herein by reference. The mask may also include an exchangeable two mask system such as the FDA cleared AF541 mask by Respironics (Murrysville Pa., USA) and masks with similar features and function such as those disclosed in US Patent Application No. 2015/0246200 to Neff, which is also hereby incorporated herein by reference.

Microphone module 100 (also referred to as "mic module") includes one or more microphone elements (also referred to as "mic elements"), in some embodiments at least two microphone elements, and is electrically coupled to an audio processing system 150, which may be part of a controller module 102 (or alternatively embedded in ventilator system 24). Controller module 102 includes a microphone control circuit 109, aerosol controller module 111, microprocessor 160, power supply 110, and amplifier 104. Microphone control circuit 109 is configured to process a speech signal from microphone module 100 and drive loud speaker 107 to amplify the patient's voice. Alternatively, the processed speech signal can output to a communications device 112 and/or headphones 114. The communication between mic module 100 and controller module 102 and/or communications device 112 may be a hard wire or wireless. The mic module 100, controller module 102 or communications device 112 can include a transceiver configured to establish a wireless connection and transmit and/or receive the speech signal. Aerosol controller module 111 is configured to drive a piezo electric element 371 in nebulizer module 350 to nebulize and deliver a medicament to a patient.

Figure 2A:
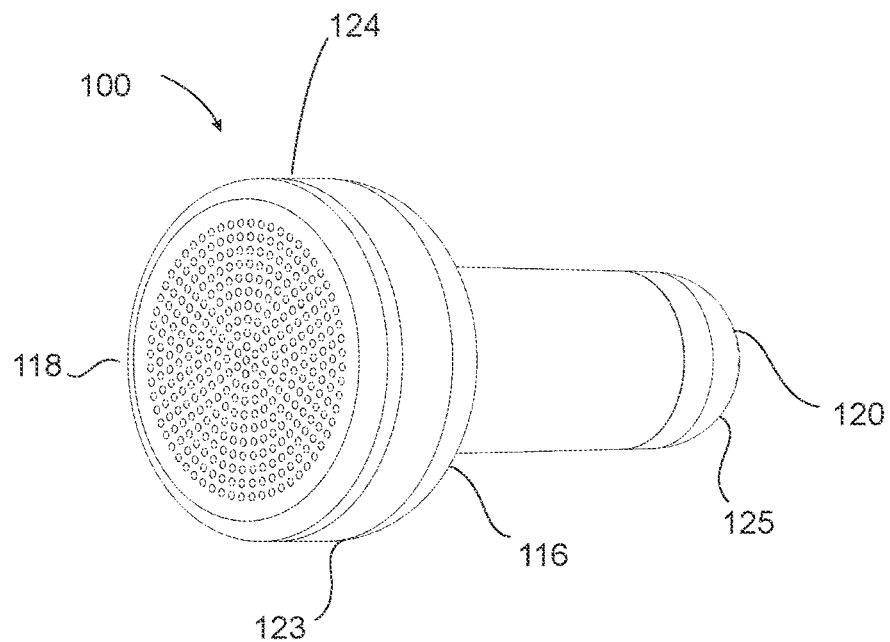
FIG. 2A is a perspective view of a microphone module according to an embodiment of the invention.
Figure 2B:
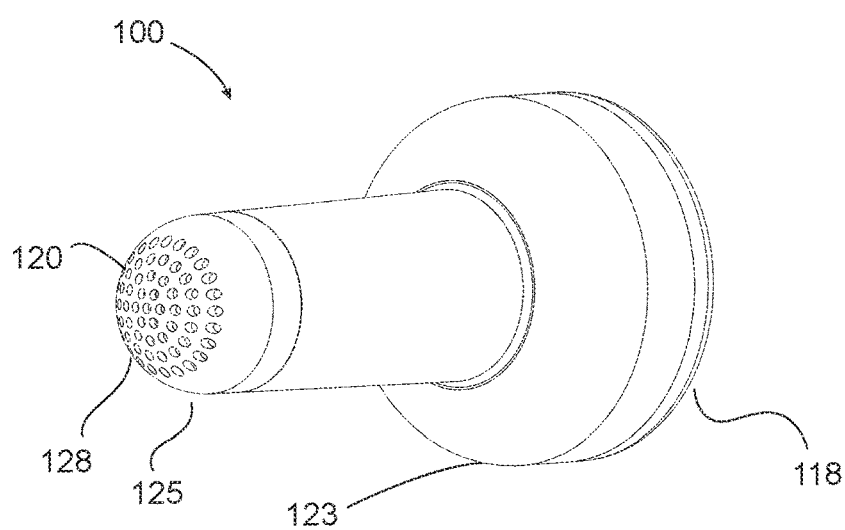
FIG. 2B is another perspective view of the microphone module of FIG. 2A.
Figure 2C:
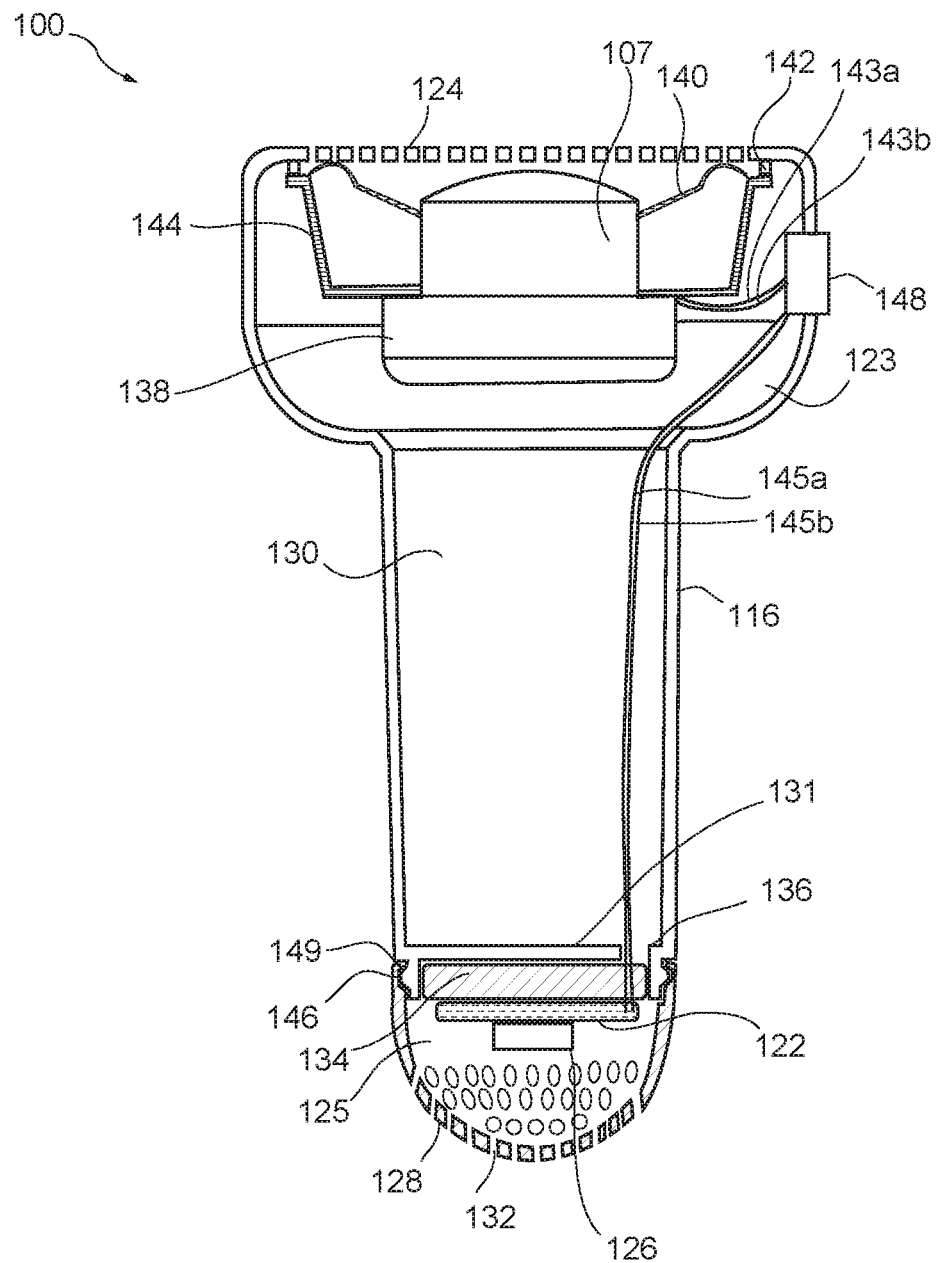
FIG. 2C is a cross section of the microphone module and FIG. 2A.

With reference to FIGS. 2A-2C, mic module 100 includes a housing 116 that extends between a proximal end 118 and a distal end 120. A portion of housing 116 forms a speaker compartment 123 that houses a loudspeaker 107, which is covered by speaker cover 124. A portion of housing 116 forms a microphone compartment 125 that houses the microphone element 126 and includes a microphone cover 128.

Loudspeaker 107 includes a frame 144 that is mounted within speaker compartment 123 using techniques known in the art. Preferably speaker 107 includes a gasket 142 that seals speaker compartment 123 from the ambient air to avoid undesired sound cancellation. Speaker 107 includes a magnet 138 and a speaker cone 148. Speaker 107 can have a diameter less than 80, 60, or 50 mm and greater than 15, 20, 25, 30, or 40 mm or within a range of any of the foregoing endpoints. Speakers with a diameter less than 50 mm are particularly preferred. The speaker 107 may have a maximum power input of 0.5, 0.1, 2, 5, or 10 watts and/or less than 10, 15, or 10 watts or within a range of the foregoing endpoints.

Speaker 107 is electrically coupled to a female connector 148 through wires 143a and 143b (collectively wires 143). Female connector 148 is configured to receive a cable connector to receive the processed audio signal to drive loudspeaker 107, thereby amplifying the patient's voice. Connector 148 can be configured to transmit power, audio, and a plurality of mic signals.

Speaker compartment 123 preferably extends into the hollow tubular portion 130 of housing 116. Tubular portion 130 extends to rigid wall 131 and provides significant back volume to speaker 107. The portion of the speaker compartment 123 that extends from loudspeaker 107 to wall 131 forms a back cavity (i.e., the void behind the speaker). In a preferred embodiment the back cavity includes a back cavity foam (not shown) for increasing the apparent back volume of speaker compartment 123. Back cavity foam can be placed into tubular portion 130 adjacent wall 131 and can fill any portion of the cavity. In a preferred embodiment the back cavity has a volume of at least 10, 15, 20, or 25 ml and less than 80, 60, 50, or 40 ml, or within a range of the foregoing endpoints.

In a preferred embodiment, housing 116 is configured such that at least a portion of the back cavity is positioned on an inside of mask 10 (including the inside of the elbow 26). Using the space within the mask to provide back volume reduces the bulkiness of the microphone module and positions its center of gravity closer to the mouth, which avoids creating pressure on the mask and pressure sores that can be caused by the mask.

Microphone compartment 125 includes a circuit board 122 positioned on vibration dampening material 134. Vibration dampening material 134 minimizes undesired vibrations from speaker 107, which can cause undesired feedback noise. Material 134 can be mounted on wall 131. Preferably wall 131 is rigid so as to avoid the speaker pressure changes causing the wall to move, which could then move the microphone and cause undesired distortions or feedback. Material 134 dampens vibrations between wall 131 and circuit board 122. Material 134 may be less than 1, 0.5, or 0.25 inch and greater than 0.1, 0.2, or 0.3, or 0.5 inch and/or within a range of the foregoing endpoints. Material 134 may have a durometer greater than 30, 40, 50 and/or less than 80, 70, or 60. The material may have an oval, circular, or ring shape. The material is preferably a visco-elastic material and may be a thermoset polyurethane.

Circuit board 122 electrically couples microphone element(s) 126 to connector 148 through wires 145a and 145b (collectively wires 145). Wires 145 may pass through hole 136 up to connector 148. Hole 136 should be sealed to air (e.g., using an adhesive or gasket) to prevent sound feedback from speaker 107 to microphone element 126. Connector 148 provides an electrical connection to controller module 102 through a wire/cable.

In an alternative embodiment, wall 131 may be removed and circuit board 122 sealed to the walls of tubular portion 130 using a vibration dampening o-ring or gasket. The microphone elements may be positioned inside tubular portion 130 with a hole facing compartment 125 or may be positioned on the circuit board within compartment 125.

Microphone elements 126 can be an electret or a MEMS. The microphone element may be a condenser mic and/or require phantom power. The phantom power may be in a range from 2-10 volts, preferably 3-5 volts. The microphone element may be an omnidirectional microphone or a directional microphone, but omnidirectional is preferred. Preferred microphone elements have a high dynamic range and/or high sound pressure level. Digital MEMS (a/d converter on mic board) are also suitable, which can be used to reduce electrical noise from hospital equipment placed near the bedside. Digital MEMS may also be useful for having more microphone elements with fewer wires since the signals from different elements can be transmitted on the same wire. In some embodiments, the microphone element may be an active mic (power sent to the mic). The microphone element may also have its own pre-amp before the preamp in the audio processing system. A pre-amp on the microphone can reduce clipping of the microphone, which can be a particularly difficult problem with voice amplification on positive pressure masks due to the increase in pressure. Although not preferred, some embodiments can use a single microphone element. Noise cancellation with a single microphone element can require additional computation power. Noise cancellation can be performed using the frequency domain to identify non-speech elements of the signal.

The one or more microphone elements may be mounted with the active surface facing the mouth of the patient (i.e., parallel to board 122) or off axis (e.g., perpendicular) so as to avoid direct sound pressure from the mouth.

Preferred embodiments of the system use two or more microphone elements. The two or more elements can perform processes upon coincident signals are useful, such as in discriminant noise cancellation. Two microphone elements may be mounted on a board and/or within housing. The microphone elements may be differently specified microphone elements or preferably identical specification mic elements. The mic elements may be mounted in the same plane, off plane, and/or at different angles. Same plane microphones may facilitate manufacturing while differently angled microphones may provide better discernment of off-axis signals. Detecting off-axis signals can facilitate detecting incoherent (e.g., turbulent) sounds as opposed to coherent.

In a preferred embodiment, the microphone has a relatively high max sound pressure level. The closeness of the microphone in the mask and the relatively high pressure in the mask causes surprisingly high sound levels even for patients talking moderately loud or quietly. The microphone module may include a sound attenuating material configured to create an effective sound pressure level that avoids microphone clipping for a person talking at 50, 60, or 70 db. For purpose of this invention, unless otherwise indicated, effective sound pressure level is the sound pressure level of the microphone plus the decibels by which the sound attenuating material attenuates sound. The sound attenuating material may have a thickness and/or a density that prevents clipping of a microphone in the housing when placed in the mask. The sound attenuation of a foam may depend on its density and thickness. The density and thickness may be selected to reduce peak sound pressure on the microphone element by at least 5 db, 10, db, 20 db, 30 db, 40 db, or 50 db and/or less than 60 db, 30 db, or 20 db, or within a range of the foregoing.

In some embodiments, the microphone element 126 may be a MEMs device with differential non-inverting analog output. The differential signal can be used to reduce induced noise caused by transmitting the microphone signal and the processed signal (i.e., amplified signal) within the same electrical cord. Alternatively, the audio processing system 150 may have a differential signal generator. The mems device may have an always on low power mode. The low power mode may be used for speech detection and noise cancellation. The low power mode may be configured to use less than 100, 80, or 60 microamps and/or more than 1, 10, or 40 microamps or within a range of any of the foregoing endpoints.

An example of a suitable electret may have the following specifications plus or minus 5%, 10%, or 20% for any: −42±3 dB RL=2.2 kΩ Vcc=2.0 v (1 kHz 0 dB=1 v/Pa) Impedance Max. 2.2 kΩ 1 kHz (RL=2.2 kΩ) Frequency 50-12000 Hz Current Consumption Max 0.5 mA Operating Voltage Range 1.0-10 V Max SPL (dB) 120 dB S/N Ration More than 58 dB Sensitivity Reduction 2.0-1.5V Variation less than 3 dB Storage Condition −20~+60° C.; R.H.<45%~75% Operating Condition −10~+45° C.; R.H.<85%.

In a preferred embodiment the microphone element has a diameter less than 0.8, 0.5, 0.3, 0.25, 0.2, 0.15 and/or greater than 0.03, 0.05, 0.1, or 0.15 inch and/or within a range of the foregoing. The microphone elements may be a directional microphone or an omni directional. Microphone elements 126 are selected to have a low self-noise, a high max SPL, and/or a high dynamic range and/or a small size. For purposes of this invention, the SNR is measured with a standard reference pressure of 94 dB SPL (1 Pa) at 1 kHz. In one embodiment, the dynamic range is at least 80 db, 85 db, 90 db, or 95 db, the SNR is at least 60, 65, or 70 db and/or the sound pressure level of the microphone element is at least 80, 85, 90, 95, 100, 105, 110, 115, 120 and/or less than 160, 150, 140, 130 or within a range of any of the foregoing endpoints (at the conditions set forth above for the suitable microphone element).

The microphone cover 128 includes features to transduce voice. In some embodiments, cover 128 may include a plurality of holes (e.g., hole 132) or alternatively be made of a wire mesh. cover 148 can snap fit onto the housing of tubular portion 130 using snap fit features 146 and 149 on cover 128 and tubular portion 130, respectively. Alternatively cover 128 can be user removable and/or replaceable. For instance, cover 128 may screw on. The user replaceable cover allows the cover 128 and if present, the attenuator, to be replaced if it becomes soiled. The attenuator can be adhered to cover 128 to ensure proper fit and placement.

Module 100 can include an attenuator (not shown) within compartment 125. Attenuator 125 can fill a portion or all of the space within compartment 125 between microphone element 126 and cover 128. Placing the microphone element close to the patient's mouth can cause excessive gain or clipping of the microphone. To reduce the power of the vocalization, a sound attenuating material can be placed between the mic elements and the mouth of the patient. The sound attenuating material may be a dense or thick foam. A high dynamic range microphone placed near the mouth and attenuated can produce a signal that is suitable for processing in a digital signal processor. In one embodiment the attenuator may be a foam with a density of at least 2, 2.5, 3, 4, or 5 lb ft3 or less than 10, 8, 7.5, 7, or 6 lb ft3. In a preferred embodiment, attenuator is a biocompatible foam. Traditional foam windscreens typically have a density less than 2 lbs ft3, has been found to not be sufficient to attenuate the power of the voice when using a high dynamic range or high max SPL mic placed near the mouth in a PPV mask. In one embodiment, the attenuator reduces the sound pressure level across the attenuator by at least or less than 3, 5, 10, 12, 15, or 20 db or a range thereof.

Configuring microphone module 100 with loudspeaker 107 is highly advantageous because during use the amplified speech has the perception of coming from the patient, which will sound more natural. More natural speaking can be important to critically ill patients since they are frequently at end of life and desire to communicate with loved ones for the last time. In addition, providing a patient with voice amplification can be important for compliance and patient comfort. If the patient can hear themselves talk they can relax because the sound is as expected. If the sound is muffled the patient naturally tries harder to make more sound even if such effort is not necessary.

In a preferred embodiment, the microphone module is configured to be single patient use to prevent contamination between patients. However, the controller module 102, which does not directly contact the patient may be configured to be reusable between patients. For example, the controller module may include a clamp or bracket for being attached to a ventilator or bed rail. The controller module 102 is preferably attached to the ventilator or integrated into the ventilator to avoid accidental disposal by a clinician.

Figure 3:
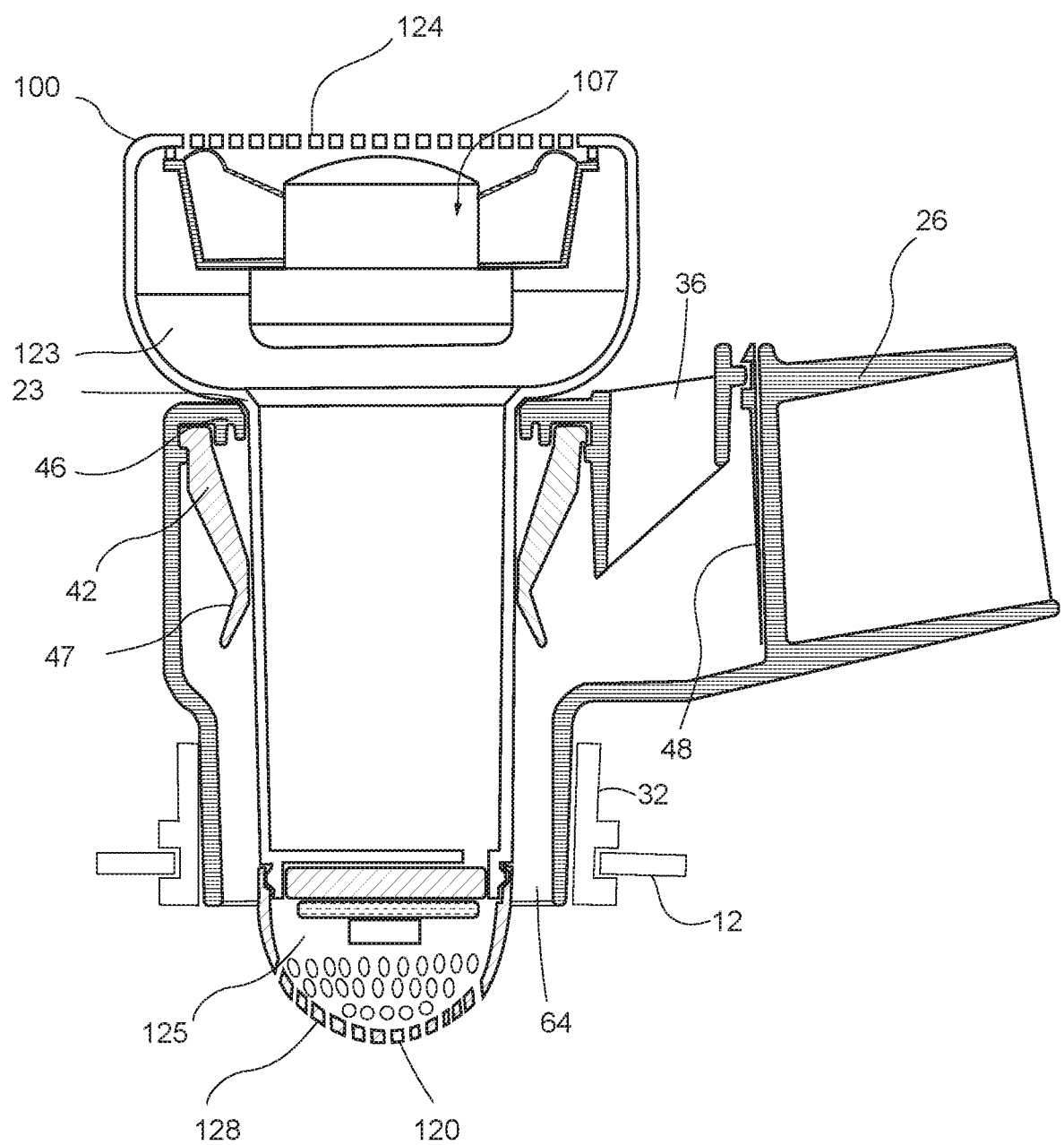
FIG. 3 is a cross section of the microphone module of FIG. 2A inserted into the elbow of FIG. 1A.

FIG. 3 is a cross section of mic module 100 inserted into mask 10 through elbow 26. Mic module 100 has its distal end extending through shell 12 of mask 10 toward the mouth of the patient. Mic module 100 is positioned in the access port 23 which extends from ring 46 to opening 64 of elbow 26. Inserting microphone module 100 into port 23 opens duckbill valve 42. The cross slit in duckbill valve causes the distal end 47 of valve 42 to flare out. This flare is advantageous for avoiding inverting valve 42 when removing module 100.

Housing 116 forms an adapter with a shape configured to form a PPV seal with ring 46 of elbow 26. The external or outside portion of module 100 extends from ring 46 to proximal end 124 and is exposed to the ambient. The internal or inside portion of module 100 extends from ring 46 toward distal end 120 and is exposed to the pressure of the ventilator. Due to the shape of valve 42, it typically does not form a seal around tubular portion 130 when microphone module 100 is positioned for use. Upon removing microphone module 100 valve 42 returns to its sealing position under ventilator pressure.

Microphone module 100 extends beyond opening 64 so as to place the microphone beyond mask body 12 and its adjacent structure (e.g., swivel 32). Moving the microphone beyond opening 64 and/or away from shell 12 has been found to substantially improve the signal to noise ratio. In one embodiment, housing 116 is configured to couple with the access port and place the distal end of microphone module at least 0.25, 0.5, 0.8, or 1.2 inch inside the mask from the center point of opening 64 (i.e., the inside opening of the access port). Preferably the microphone element 126 is positioned less than 3, 2, 1.5, or 1 inch and/or greater than 0.25, 0.5 or 1.0 inch and/or within a range of the foregoing from the opening 64. The length of the housing as measured from the position on the housing that engages the access port (i.e., forms the PPV seal) to the distal end (i.e., the oral end) of the microphone module may be greater than 1, 1.5, 2, 2.5, 3 inch and/or less than 6, 5, 4, 3.5, 3, 2.5, or with a range of the foregoing (i.e., the length of the tubing from where the tubing forms a seal with the mask and the distal end).

FIG. 3 also shows a valve 42 with a small upper rim that is pinched between an annular rim and a narrow seat. The annual rim on the ring 46 allows for the rim to be very small while resisting pull out. The overlap of the seat and the rim may be less than 3, 2, or even 1.5 mm and/or greater than 0.75 mm, 1, or 1.2 mm or within a range of the foregoing endpoints. The small rim can have a substantial impact on the overall size of the elbow.

Figure 4:
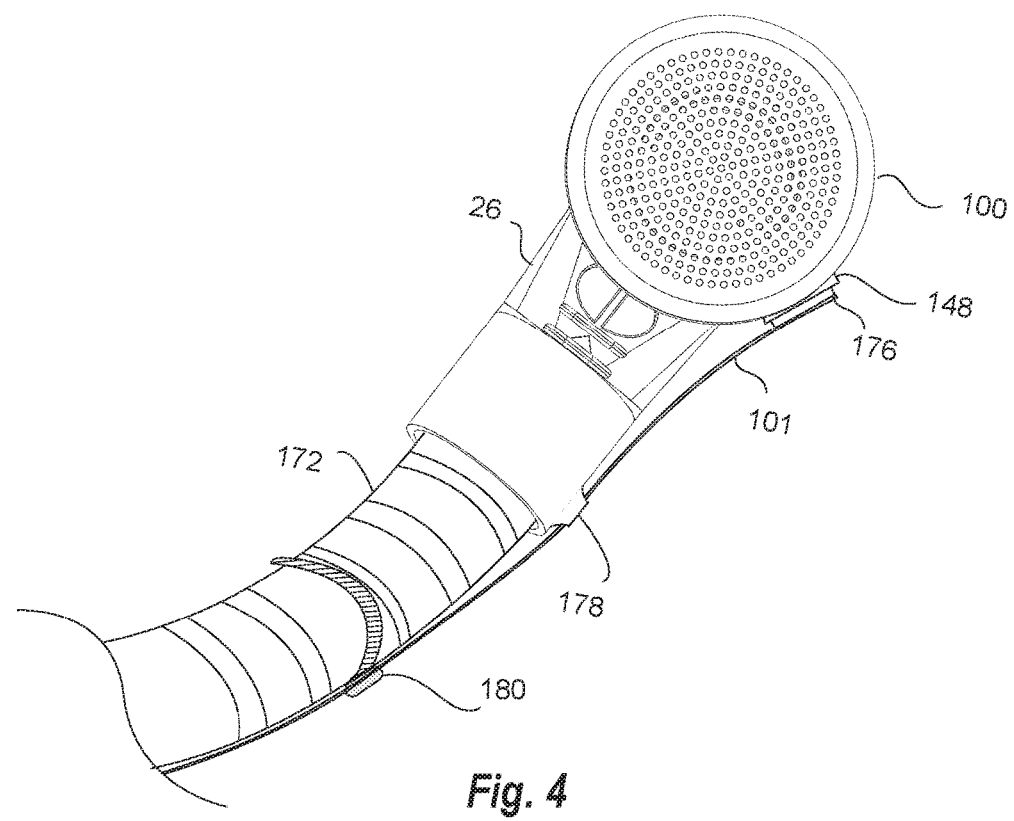
FIG. 4 is a top view of the microphone and elbow of FIG. 3 and a ventilator hose and electrical cable.

FIG. 4 shows a top view of microphone module 100 inserted into elbow 26 with a flexible ventilator tubing 172 attached thereto. Cable 101 has male connector 176 that is removably coupled to female connector 148 of microphone module 100. connector 176 is preferably an angled connector so as to allow the connector to be positioned on a side of elbow 26, which avoids the cable crossing over opening 36 of the anti-asphyxia valve. The angle may be greater than 30, 45, or 60 degrees and may be a right-angle connector. An angled connector also allows the cable to be unplugged by pulling transverse to the axis of cable 101, which runs parallel to tubing 172. The transverse orientation avoids the need for slack in the cable or pulling the cable in the axial direction. Elbow 26 can include fitting 178 configured to removably receive the cable by pressing the cable into fitting 178. Alternatively, or in addition, cable 101 can be secured to ventilator tubing 172 using clip 180. Clip 180 removably clips to ventilator tubing 172 and secures wire 101 between clip 180 and tubing 172.

In some embodiments, cable 101 can be used to power more than one device. For example, connector 176 can be removed from connector 148 and microphone module removed and a second device (e.g., nebulizer) inserted into elbow 26 and connected to the same cable 101 using connector 176. This configuration avoids the need to run different cables along ventilator tubing 172. In some embodiments, the electrical configuration of the microphone module and the nebulizer may indicate to the controller module 102 which of the two devices is electrically coupled. The configuration can be achieved with a short of a pin or using a small chip that provides an identifier. The identifier can then be used to configure the controller module 102 or ventilator unit 21. For example, the controller module 102 or ventilator unit 21 may have particular modes of operation or user interfaces that are specific to the device being used (e.g., microphone vs. nebulizer).

The present invention also relates to adapters, appliance modules and methods for nebulizing a patient on non-invasive positive pressure ventilation (PPV). The nebulizer adapters and nebulizer appliance modules of the present invention can deliver aerosols to the oral cavity of an PPV patient while maintaining pressure and without disconnecting the ventilator circuit to attach the nebulizer.

In a first embodiment, a nebulizer appliance module 350 is configured to be inserted into an access port 23 and/or a valve 42 of a PPV mask 10. Tubular portion 362 is sized and configured to be re received by ring 46 of elbow 26 and form a PPV seal therewith. Tubular portion 362 may have a diameter 374 that allows tubular portion 362 to form a seal. In one embodiment housing 352 includes wall 376 that limits how far nebulizer module 350 can be inserted into port 23.

When the nebulizer appliance module is inserted into the mask 10 aerosol medicaments can be received directly into the mask and/or mouth of the user while receiving ventilated air in the mask. Similar to the microphone module 100, nebulizer module 350 maintains ventilation pressure in the mask while the appliance module is in use. When delivered into the mouth, less medicament will collect on the surfaces of the mask and instead a high percentage of medicament is delivered to the user.

Figure 5:
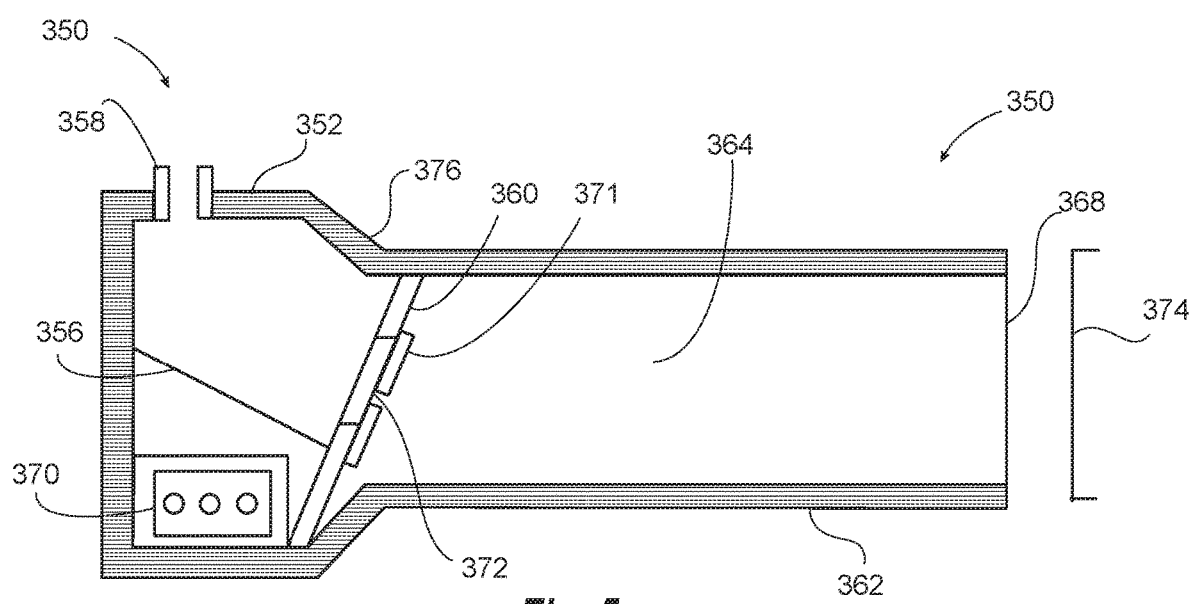
FIG. 5 shows a cross-section of a nebulizer module configured for use with elbow and electronics of FIGS. 1A and 1B.
Figure 6:
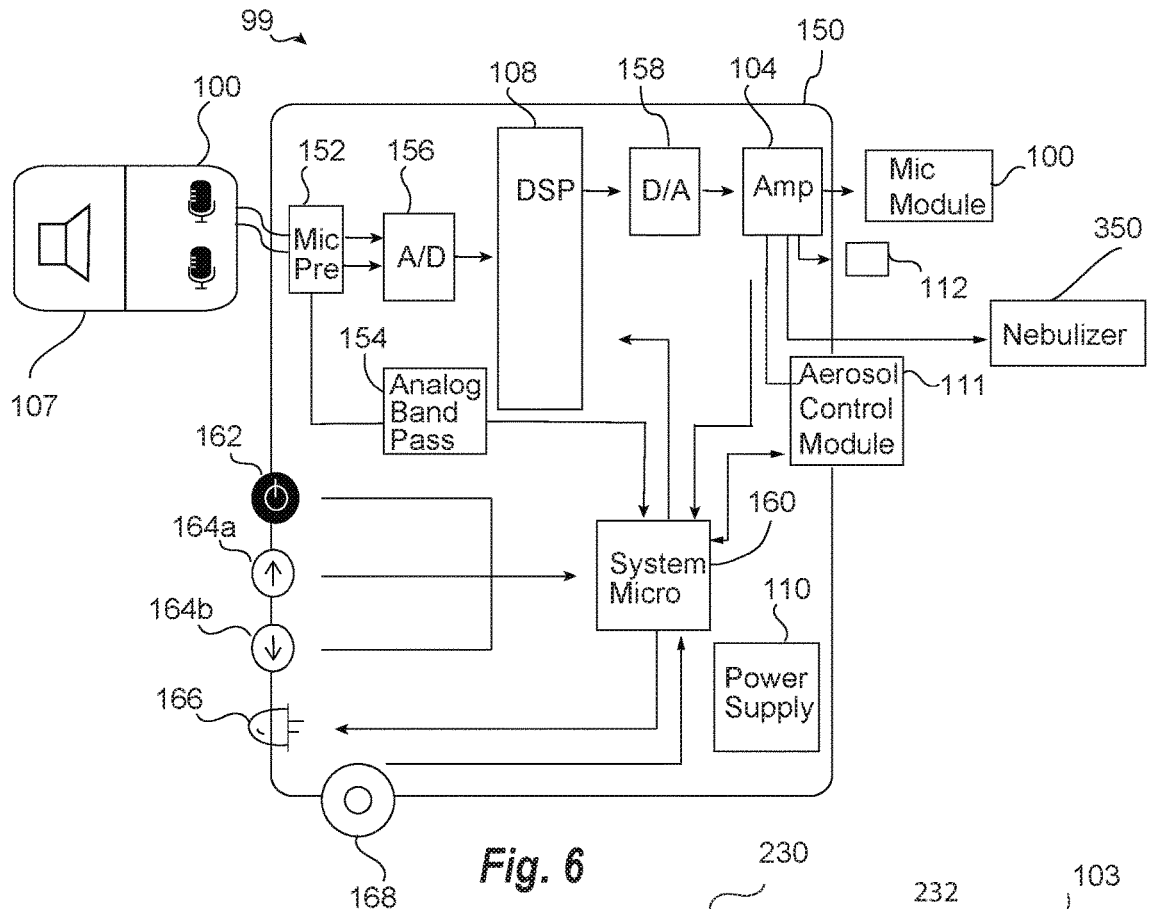
FIG. 6 is a block diagram of a signal processing system.

FIG. 5 illustrates a cross section of a nebulizer appliance module 350. The nebulizer module includes a housing 352 forms an adapter configured to be inserted into port 23 of elbow 26 and form a seal with ring 46. The housing 352 also defines a fluid reservoir 354 with wall 356 and aerosol generator 360. Reservoir 354 is in fluid communication with inlet 358 and a vibratable member 372 (such as a micro vibrating element) of aerosol generator 360. The aerosol generator 360 also include a piezoelectric element 371. Housing 352 includes a tubular portion 362 that defines a tubular chamber 364 that delivers nebulized fluid from the aerosol generator 360 to an opening 364. Nebulized fluid exiting opening 368 is delivered to an inside of the mask or the patient's mouth. Wall 356 and aerosol generator 360 may be placed at an angle relative to the longitudinal axis of tubular portion 362 to ensure that during use drug flows toward aerosol generator 360.

Reservoir 354 can hold a liquid volume of at least 2 ml, 4 ml, 6 ml, 8 ml, or 12 ml and/or less than 50 ml, 30 ml, 25 ml, or 20 ml, and/or within a range of the forgoing endpoints.

Nebulizer module 350 also includes a female connector 370 for receiving cable 101 and electrically coupling nebulizer module 350 to controller module 102. The aerosol generator is at or near to the distal end of the adapter body 252 and is in fluid communication with the inner fluid reservoir 254.

Nebulizer module includes a connector 370 that can removably receive a connector on a cable. In a preferred embodiment, nebulizer connector 370 is configured similarly to microphone module connector 148 and can receive male connector 176 of cable 101. By sharing the same connector configuration, microphone module 100 and nebulizer module 350 can utilize the same cable and be controlled by controller module 102 using the same cable 101.

Controller module 102 is configured to output an aerosol generating signal to operate aerosol generator 360. The controller module causes the piezoelectric element 371 to vibrate the vibrating member 372. This vibration of the vibratable member 372 causes the liquid medicament to pass through the apertures of the vibrating member 372 (e.g., move through the holes in a mesh) where the medicament is aerosolized by the ejection of small droplets of medicament. The aerosolized droplets of medicament flow through tubular chamber 364 and exit into the oral airway to be received by the respiratory track of the user.

FIG. 5 illustrates a simplistic view of a nebulizer circuitry, parts, and connections. See U.S. patent Ser. No. 10/833,932 for a detail description of the circuitry, parts, and connections of a micro aerosol generator system, which is hereby incorporated herein by reference. Additional details about suitable nebulizer modules that can be used in combination with the present invention are disclosed in applicant's U.S Patent Publication No. US 2019/0091434 and co-pending application Ser. No. 16/101,379, both of which are hereby incorporated herein by reference.

FIG. 6 illustrates an example hardware design for an audio processing system 150 suitable for use in voice amplification system 99. System 150 includes a microphone preamplifier 152, an analog band pass filter 154, an analog to digital converter 156, digital signal processor 108, digital to analog converter 158, power amplifier 104, system microprocessor 160, power supply 110, power on/off switch 162, volume up and down buttons 164*a* and 164*b*, power indicator LED 166, aerosol control button 168, and an signal output 112.

System 150 receives at least one microphone input from microphone module 100 (preferably a plurality of microphones inputs). Each audio signal is gain adjusted in microphone preamp 152 and then converted to a digital signal using analog to digital converter 156 and/or output to analog band pass 154. The digital signal is then processes using digital signal processing 108 and converted back to analog using digital to analog converter 158. The processes analog signal is amplified using power amplifier 104 and output to a loud speaker 107 or another communication device 112, such as desktop computer, laptop computer, mobile phone, or the like.

The communication device 112 may include communication software that initiates a phone call or messaging service to transmit the processed voice signal to a remotely located person, thereby allowing communication between the patient and the remotely located person. The communication software may include a voice to text converter for converting a patient's voice to text and communicating the text to the remotely located person.

Analog band pass can be used for detecting voice signals and the detected voice signals can be used by system microcontroller 160 to turn on components of the system (e.g., DSP 108).

All or portions of the components of system 150 may be housed in a stand-alone enclosure, the microphone module 100, a speaker enclosure (e.g., controller module 102 (FIG. 1B), communication device 112, headphones 114, ventilator unit 21 (FIG. 1B), or combinations of these (e.g., pre-amp in module 100, DSP 108 in communication device 112 or in ventilator unit 21).

System microcontroller 160 can be used to receive input from volume buttons 164 and/or power button 162. The system microcontroller can provide output such as through LED 166 to indicate the state of the system or other information (e.g., on, off, standby, voice detected, an error, low battery, adequate battery, etc.).

Aerosol controller module provides a control signal that is amplified by amplifier 104 and to control aerosol generation in nebulizer module 350. nebulizer control button 168 allows a user to provide input for starting nebulization and/or selecting a mode for nebulization.

System 150 may also include circuitry for processing feedback noise. Vibrations from speaker 107 can create a signal in microphone element 126 that can cause feedback noise. The feedback processing can use filtering (e.g., notch filtering) to reduce or eliminate the feedback loop noise. Examples of audio processing systems that can be used with the present invention include systems described in U.S. Pat. No. 7,602,925 to Kreifeldt, which is hereby incorporated herein by reference.

Controller module 102 may be housed in a housing and include a bracket for attaching the housing to a bedrail or a ventilator. For example, the housing may attach to a screw clamp that can be connected to a mounting bracket or rail on a ventilator. FIG. 1D is a block diagram showing controller module 102 including an attachment mechanism 311 with a screw mount 313 in the housing of controller module 102 and a clamp 315 configured to clamp to a rail of a ventilator.

FIG. 7 is a flow diagram 103 illustrating audio signal processing 103, which can be carried out for example on DSP 108 (FIG. 1B). The audio signal from mic inputs 220*a* and 220*b* are each processed using a band pass filter and frequency equalizer 222. The band pass filter can be used to cut out frequencies outside speech. In some embodiments, the band pass can filter out frequencies less than 300, 250, 200, 150, or 100 and/or greater than 3000, 3400, 4000, or 5000, and/or within a range of any of the foregoing. The mic EQ can be used to correct non-flat microphone response. In one embodiment, the mic EQ is used to correct a non-flat signal caused by an NIV mask. The frequencies passed by the band pass filter may be equalized to produce a more even sound across the range of frequencies. The frequency equalization typically corrects variation created by the microphone elements and is often specific to the particular microphone being used and its configuration in the mask housing mask.

The audio signal is then processed using noise reduction block 224. The noise may be incoherent (e.g., turbulent) sounds produced within the PPV mask or sounds that are off axis from the speech sound. Incoherent sounds typically include wind noise (created in the mask), ventilator noise (piped down tube or vibration from outside mask), ambient noise (beeps, alarms, non-voice ambient sounds) self-noise (noise floor or white noise). Noise reduction block can compare mic inputs 220*a* and 220*b* and detect the amplitude and phase. Sound that is out of phase and has a high amplitude can be indicative of noise generated from incoherent sounds. The incoherent sounds are then attenuated to remove the noise from the audio stream. Out of phase noise is best detected using dual microphones (preferably identical microphones) positioned spaced apart and near each other and positioned in the same plane. Alternatively, and less preferred, a single microphone signal can be analyzed for characteristics that are indicative of incoherent or turbulent noise (e.g., analyzing frequencies and/or envelope characteristics), which is then used to attenuate the noise.

The audio stream generated in an NIV mask has been found to have noises that cannot be eliminated using the foregoing dual mic noise reduction techniques. NIV masks can create breathing noises (inhalation and exhalation) where a significant portion of the noise is coherent with speech and/or are non-turbulent. These breathing noises have a pronounced un-natural sound (similar to the breathing by Darth Vader in the movie Star Wars). The present invention relates to audio processing systems that can remove these noises using a patient activity detector. Digital signal processing 103 includes an activity detector that detects patient activity such as breathing or speech and then uses the detected patient activity to attenuate the noise. The DSP patient activity detector can also be used to reduce power usage in the microphone system and/or to adjust settings on the ventilator.

A side stream 226 of the audio stream is processed in patient activity detector 230. Activity detector 230 can include speech activity detector and/or breathing activity detector 234. Side stream 226 splits from main audio signal 228 so that activity detector 230 can remove portions of the speech to detect the activity even if removing those portions of the stream are also important for maintaining a natural sounding voice (i.e., the main audio stream retains the portions of the speech removed for activity detection). The output from activity detector 230 is then used by speech admitter 236 to selectively pass the main audio signal 228. Alternatively, the detected activity may be used by system micro 160 (e.g., to power down amplifier 104) or outputted through activity out 238 to a ventilator 21 or other device.

FIG. 8A illustrates an example circuit for performing activity detection according to one embodiment of the invention. Side stream 226 is split and processed using band pass filter 248 and band pass filter 249. Band pass filter 248 aggressively filters out portions of the voice data and passes particular frequencies that are indicative of speech and breathing (breathing in and/or breathing out). The band pass filters can be the same or different. The band pass filters can be an infinite impulse response filter or a finite impulse response filter. The IIR filter may be a direct form I or II, preferably a direct form I as shown in FIG. 8B (circuit 262). Band pass is performed using a cascade of at least two of the direct form I filters shown in FIG. 8B. In a preferred embodiment, $b_0$, $b_1$, $b_2$, $a_1$ and $a_2$ are $2^{nd}$ order Butterworth filter. In some embodiments, the band pass filter is an at least second order filter, more preferably at least $4^{th}$ order filter or a $6^{th}$ order filter. The band pass filter is used to produce a frequency of interest. For example, band pass filter can be used to attenuate frequencies that are outside a frequency range of interest for detecting speech or breathing. The band pass filter may be placed before power envelope 250, RMS 252, or both, or other components of the circuit. The band pass filter can include a plurality of band pass filters and/or split the audio stream and perform on two or more portions of the audio stream. The activity detector may filter out parts of the speech signal to isolate frequencies that are unique to speech and/or unique to breathing. In some embodiments, the band pass filter of the activity detector is configured to attenuate all or a portion of the speech frequencies less than 150, 250, 300, 400, 500, 1000, or 2000 hz and/or greater than 5000, 4000, 3000, 2000, or 1000 hz, or within a range of the foregoing endpoints. In some embodiments, the bandpass filter removes the first harmonic, or second, more preferably the third or fourth harmonics and passes the speech fundamental and/or the first harmonic. In some embodiments the bandpass removes the fundamental frequency and lower harmonics and passes only the upper harmonics.

Once side stream 226 has been processed in the band pass filter, signal 226 is then processed in power envelope block 250 and root mean square block 252. The RMS is a long-term average power of the signal. The power envelope is a short-term average power of the signal. The power envelope is somewhat equivalent to a smoothing of the envelope. FIG. 8C describes a digital RC filter 264 that can be used in the present invention to determine power envelope 250 and/or RMS 252. The RC filter 264 may be an integrator circuit where alpha+beta=1 and if $X(n)>y(n)$, alpha is =alpha1 B=B1 else alpha=A2, beta=B2. For the power envelope 250, the alpha coefficient is set high (e.g., greater than 0.5, 0.8, or 0.9) and for the RMS 252, the alpha coefficient is set low (e.g., less than 0.5, 0.2, or 0.1). RMS 252 can use a plurality of RC circuits having different coefficients to achieve a stronger signal for a given average time.

Figure 8D:
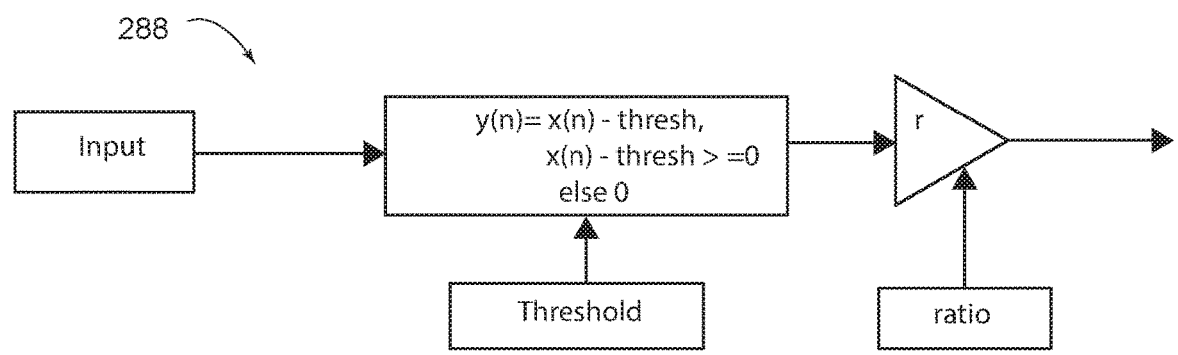
FIG. 8D describes a threshold filter of FIG. 8A.

FIG. 8D describes a threshold filter 288 that can be used in the present invention to select a threshold. For example threshold filter 288 can be used for the threshold of voice 254, threshold of breathing 256, or threshold of no signal 258 as shown in 8A.

The difference between power envelope 250 and RMS 252 in combination with the RMS produces three states that indicate breathing noise, speech, or no activity, respectively. If the difference between power envelope and RMS is high, and the RMS is high, then threshold for voice will be greater than zero and the threshold for "no signal" is 0, which is indicative of speech. If the difference between the power envelope and RMS is low and the RMS is high, then the threshold for breathing is greater than zero and the threshold for "no signal" is zero, which is indicative of a breathing noise. If the RMS is low, then threshold for no signal is greater than zero, which is indicative of no signal. The signals for speech, breathing, and no activity can be passed through a threshold circuit to allow probabilities to be associated with each signal prior to being integrated in comparator 260. The comparator receives the signals from the threshold circuit and produces the returned state of the patient activity (speech activity, breathing activity, or no activity).

The alpha and beta coefficients used for the power envelope 250 and RMS 252 can be selected to set a time average of the signal. In one embodiment, the power envelope is averaged over a period of time of at least 0.25, 0.5, 1, 5, 10 ms and/or less than 30, 20, 10 ms, or with a range of any of the foregoing endpoints. In some embodiments, the RMS of the signal is averaged over a period of time greater than 3, 5, or 10 ms and/or less than 250, 100, or 50 ms, or with a range of any of the foregoing endpoints. In some embodiments, the time average for the RMS is at least 3, 5, 10 times greater than the sampling time for the power envelope and/or less than 250, 100, or 50 times the sampling time for the power envelope, and/or within a range between any of these endpoints.

Admitter 236 has a gain element that opens or closes to attenuate or pass signal 228 through admitter 236. When speech is detected the gain element opens and signal 228 passes. When no speech is detected or when breathing noise is detected, the gain element closes and signal is blocked. Admitter 236 may have a small delay to allow for speech detector to process the signal. Delay is preferably less than 40, 20, 10, or 1 ms. Admitter may have a ramp between beginning and ending changes in the level of attenuation. The ramp may be less than 20, 15, 10, 5, or 1 ms and/or greater than 0.01, 0.05, 1 ms, and/or within a range of the foregoing endpoints. The ramp may be exponential or linear. Ramping can be important for naturally sounding speech. If ramping is too slow, the sound will be chopped off. If ramping happens too quickly, the sound can pop.

In an alternative embodiment, speech admitter 236 can receive a breathing activity signal from ventilator 21. In this embodiment, a pressure senor in the ventilator circuit detects negative pressure indicative of inhalation. The negative pressure activity can be transmitted to audio processing system 150 and used by admitter 236 to attenuate the main audio signal 228. Speech admitter 236 may use the breathing activity from a pressure sensor alone or in combination with other breathing activity.

Figure 8E:
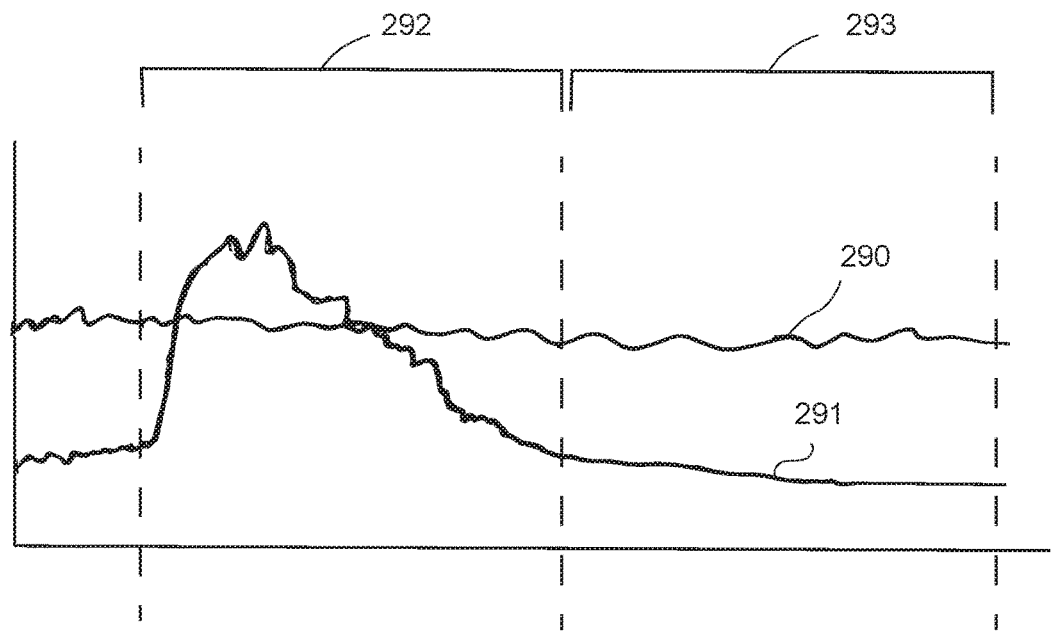
FIG. 8E illustrates breathing and speech signals in the frequency domain.

FIG. 8E illustrates a breathing signal 290 and speech signal 291 in the frequency domain (x axis is frequency and y axis is power). As shown, the breathing noise tends to be wide band and has similar power in a low band 292 and a high band 293. Breathing can be detected using low pass filtering and comparing it to a wide band signal. Since the harmonics of speech have less power, more power will be detected in the low pass filter as compared to the high pass filter for speech. Speech vs. breathing can be detected because if the signal is speech, the wide band will be not much more or similar to the low band pass. If breathing, the wide band will have substantially greater power than the low band pass.

In another embodiment, a high band pass filter is used with a wide band signal. In this embodiment, breathing is detected if the high band pass signal is similar to the wide band filter. Voice is detected if the high band pass filter is substantially less than the wide band filter.

In yet another embodiment, the low pass filter signal can be compared with the high band pass filter. If the signal is breathing, the high band pass filter will be substantially less than the low band pass filter. If the signal is speech, then the power for the high band pass signal should be substantially less than that of the low band pass filter.

Figure 8F:
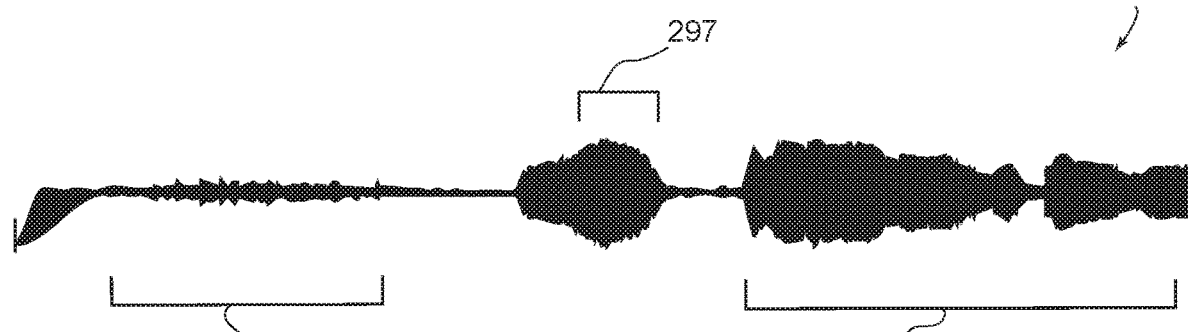
FIG. 8F illustrates breathing and speech in the time domain.

The speech activity detector or breathing activity detector may use methods other than a comparison of power envelope and RMS to detect speech and/or breathing activity. In order for the detection to be fast it can be advantageous to perform signal processing that is based on crest factor features. Speech tends to have a high crest factor and breathing noises tend to have a low crest factor. FIG. 8F shows a time domain signal 294 with a breathing noise 295 and speech 296. The breathing noise produces a longer flatter signal 295 as compared to speech 296. The flatter signal can be identified by its crest factor, which will be lower over the short term and long term as compared to speech. Speech on the other hand may have a high crest factor. The envelope of speech changes rapidly over short periods of time whereas breathing noise has an envelope that changes more gradually over the same amount of time. In some embodiments, processing includes calculating the number of times in a given period that the signal is above a threshold and setting a parameter for when the number of times within a period or the number of times in a row that the threshold is reached is indicative of the patient activity. In a preferred embodiment, the process is carried out in the digital domain. In some embodiments, the threshold is advantageously determined in the log domain to reduce dynamic range and discriminate the signal in the threshold filter. In some embodiments, the crest factor feature can be used to distinguish between breathing and non-vocalized consonants such as the "wh" sound or "sh" sound. These sounds can appear similar to a breathing noise over a short period of time in the time domain. To prevent false positives for breathing, the signal may be analyzed for crest factor. If the signal has a low crest factor it is likely breathing signal and if the crest factor is high, speech. The crest factor feature may be used alone or in combination the system shown in FIG. 8A. Preferably band pass filtering is performed first and if breathing is detected it is analyzed for crest factor to remove false positives.

In yet another embodiment, breathing noise and/or speech can be detected using a threshold filter with adjustable gain (e.g., buttons to allow the threshold to be adjusted up and down). The threshold filter may compare an upper cutoff to a lower cutoff and if the high pass portion of the filter is greater than the low pass portion the signal is likely breathing. Adjusting the threshold up can be useful for female voices, which tend to be higher and adjusting the threshold lower allows the system to be optimized for a male or lower voice.

In some embodiments, the digital signal processing to detect speech and/or breathing noise can include creating a plurality of filter banks over the range of speech frequencies. For example, a series of band pass filters paired with an RC circuit (FIGS. 8B and 8C) can be used to create filter banks at different frequencies. Increasing the number of filter banks allows increased discrimination between sounds that may be voice or breathing noise. Filter banks at frequencies in the 1200-3500 Hz range can be particularly advantageous to distinguish between speech and noise because speech in that range should be diminishing. Increases in signal strength in that region is indicative of noise. Typically, the number of filter banks can be between 2-20 or more. For larger numbers of filter banks (i.e., to achieve narrower bands of frequencies) Fast Fourier Transform of a particular number of points can substitute for filter banks.

Importantly, patient activity detector is not based on speech recognition. Speech recognition requires determining what was said, not just whether a human voice is active. Speech recognition would cause a delay that would require chopping the speech signal in the admitter or cause an unacceptable delay that would be perceptible to the user (e.g., greater than 80 ms). The sound being amplified in the present invention is used for communication and therefore is desirably a natural sounding voice.

Filtering breathing noise has been found to be particularly important for communication with a ventilated patient. PPV masks create problematic breathing noises that are not a problem in other settings such as pro audio. The breathing noises in the mask can be distinguished from speech based on their frequency and envelope patterns (e.g. crest factor). The breathing noise in PPV masks is substantially different compared to noises found in typical noise cancelling devices such as Bose headphones. In those devices, the noise is wide band (e.g., similar to a jet engine or shhhhhhh) and has narrow tones (e.g., constant single frequency). Breathing in an PPV mask is neither. Breathing has a shifting frequency content (shifting high low or low high) and complex tones.

Controlling Ventilator Based on Detected Activity. Some embodiments of the invention relate to controlling the ventilator using detected activity. For example, where speech is detected, the duration of the speech can be used to time iPAP in a bi-level ventilator. In some embodiments, the audio signal is collected while the patient is at therapeutic levels of ventilator pressure and the audio stream is processed on audio that was collected at therapeutic levels (ePAP, iPAP, or both).

Some embodiments of the invention relate to producing a natural sounding voice from a PPV patient by adding missing harmonic content. The PPV mask can act as a band pass filter, muffling certain frequencies such as the higher order harmonics. Some embodiments to the invention relate to identifying a fundamental frequency of speech and adding back in a missing harmonic using digital signal processor 108. In some embodiments, a missing harmonic can be added to the voice stream at a natural ratio. In this embodiment, the user may train system 150 by pronouncing a sequence of words to system 150. The training is performed with no pressure in the PPV mask. Next the user trains on the same sequence with positive air pressure. The two training sessions are used to identify a natural ratio between the person's fundamental frequency and a harmonic. The ratio can then be used to insert a missing harmonic in the user's voice at the same natural ratio from the fundamental frequency. Optionally the training may be performed at more than one pressure. In one embodiment the training happens within the prescribed therapeutic pressure(s)). The pressure may be an ePAP pressure and greater than 3, 4, 5, 8, or 12 cm H20 and/or less than 30, 25, 20, or 15 cm H20, or within a range of the foregoing endpoints. Alternatively, estimate an average ratio for particular harmonics and add the harmonic based on the estimated ratio.

Figure 9:
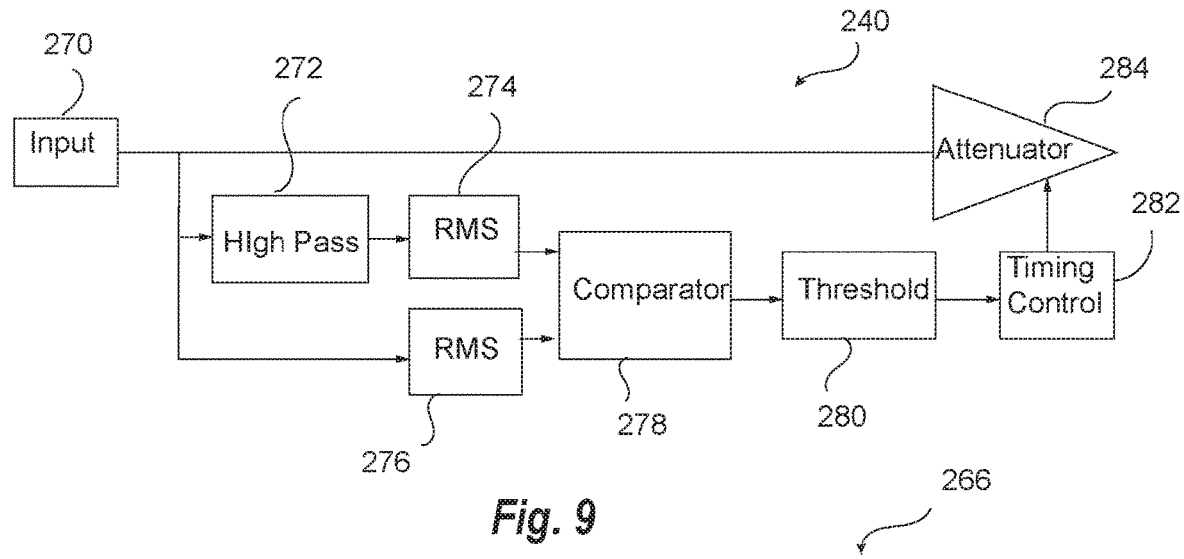
FIG. 9 is block diagram of a sibilance removal circuit.

Sibilance Removal. The present invention also relates to performing sibilance removal (block 240). Microphones placed inside the mask using a microphone module have been found to be too sensitive to "s" sounds. FIG. 9 describes circuitry for removing harsh sibilance sounds (sibilance removal 240) while maintaining a natural sounding voice. Voice input from admitter 236 is processed through a high pass filter 272. The filtered signal and the unfiltered signal are then converted to an RMS 274 and RMS 276, respectively and compared in comparator 278. When the filtered RMS 274 is comparable to unfiltered RMS 276 and reaches threshold, sibilance is relatively high and attenuator 284 is activated to attenuate the sibilance. Timing control 282 is used to delay the signal entering the attenuator to allow time for processing to occur.

Sibilance removal module can be used to allow for an improved placement of the mic near the mouth to provide an improved signal to noise ratio. The mic is placed close to the mouth in the mask, which causes disproportionately intense high frequency sounds. The de-esser attenuates the harsh high frequencies. The de-esser is advantageous over EQ because it only removes high signals when they are a problem, which means it can keep other high frequency tones to make the signal sound natural. The de-esser can use RMS (measurement of power average) to compare to power average after a high pass filter. When the two reach a threshold in equivalence, the signal is attenuated (e.g. with a VCA or filter (e.g., mic EQ). The high pass filter frequency can be selected to be between 2 k-10 k frequency. Or alternatively a male voice can be detected and the filter can be set to approximately near 3-6K or a female detected and set to approximately near 5-8 k.

Some embodiments of the invention include an auto adjust de-esser. The auto de-esser can detect male vs female voice set then set filter accordingly. Alternatively two or more fixed frequencies can be tested and then the system filters above one that is detected to have the most sibilance. Alternatively the system can scan down frequencies until the best filter frequency is found. The auto de-esser can also be carried out in the frequency domain by performing FFT on the amplitude domain and attenuate above the frequency where sibilance is occurring or EQ the signal to remove at the highest sibilance frequency.

Automatic Gain Control. In one embodiment, system 103 includes automatic gain control module 242. A particular level of gain or a range of gain is selected by the user. Module 242 monitors the RMS. When the gain falls outside the particular level or range selected by the user, module 242 adds or subtracts gain to achieve a signal within a desired range of loudness. Thus, if a clinician sets the volume of voice output (e.g., on a speaker box) and the person talks more quietly or louder in a subsequent communication, the automatic gain control module can detect a stronger or weaker signal and automatically adjust the gain up or down to match the user's selected target volume. In an alternative embodiment, automatic gain control can be used to prevent clipping from the pre-amp and maximize the signal to noise ratio. The gain is increased to a level below the max threshold (where clipping occurs). If clipping is occurring the automatic adjustment module adjusts the gain down to below the threshold. The mic preamp may be built into the DSP chip or a stand-alone chip. Automatic gain control is advantageous for NIV microphones because people that are really sick tend to talk quieter and/or have less ability to regulate the loudness of their speech. The automatic gain control allows the clinician to touch the speaker controls less frequently, which reduces potential for contamination and infection of the patient. The process can include: (i) measure short term average power of signal (i.e., window the power) (ii) select target level (i.e., how loud we want it to be around) and a noise level (iii) if signal is below noise level do nothing (you don't want to gain up/amplify noise, (iv) if signal is above noise level and below target level, add gain, and (v) if the signal is above target level gain down.

Power Management. Some embodiments, relate to managing power usage of voice amplification system 99. For example, where loud speaker 107 is battery operated, limiting power usage can increase battery life. Power usage can be minimized in several ways. In one embodiment, system micro uses output from activity detector 230 to power down various components of the audio processing system 150. For example, when activity detector 230 detects there is no speech or detects breathing noise, the system micro 160 can turn off amplifier 104. Components of system 150 can also be powered down after a particular amount of time. For example, if no speech activity is detected for a period of time, DSP 108 can be powered down and powering on may require the user to press the "on" button or activity may be detected through an analog band pass filter.

In some embodiments system micro 160 can rapidly turn on and off to perform checks for detecting voice and then power down to save power. When voice is detected, the system microprocessor 160 can turn on the power amplifier. In some embodiments, system micro 160 turns on and off a plurality of times per second.

Some embodiments relate to an analog band pass filter 154 that can be used as a low power monitor for speech detection. In this embodiment, DSP 108 can be powered down when no speech is detected and analog band pass 154 can be used to produce a wake signal that triggers system micro 160 to wake up DSP 108. Analog band pass 154 can be configured to error on the side of producing false positives for speech detection and upon waking, DSP 108 and/or system micro 160 can verify the detected speech. If speech is detected from DSP 108, power amplifier 104 can be powered.

Figure 10A:
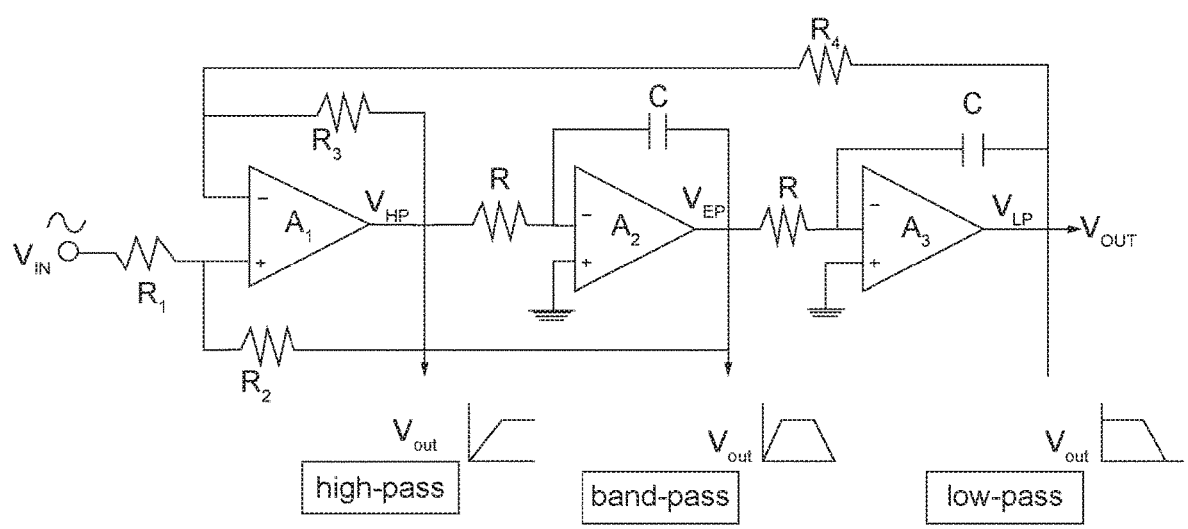
FIG. 10A-10B illustrate an analog filter used in performing an auto-on function.
Figure 10B:
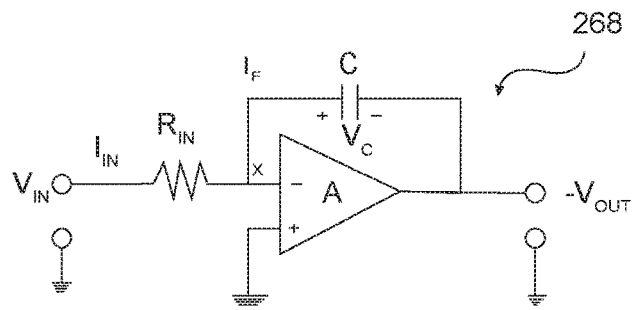

FIGS. 10A and 10B illustrate Analog band pass filters that can be used to perform an analog auto-on feature. Circuit 266 includes an analog band pass filter that isolates frequencies indicative of speech. The analog comparator 268 shown in FIG. 10B can be used to compare frequencies for determining speech vs. noise.

Speaker equalization 244 can be performed on the processed signal to flatten the signal for a particular speaker or enclosure.

In a final step 246, the audio signal is output for amplification and playback on a loudspeaker.

The present invention also relates to digital signal processors that are housed within a microphone module, a speaker housing, a stand-alone housing, or a ventilator. The speaker may be a traditional cone based speaker, or an exciter.

In some embodiments, the signal processing can be carried out in software on a mobile phone. The microphone may be attached to a mobile phone and processed using the mobile phone processor as described herein with regard to DSP 108. The output may then be transmitted over a mobile phone and/or played on a loud speaker (e.g., headphones) to a user.

Figure 11A:
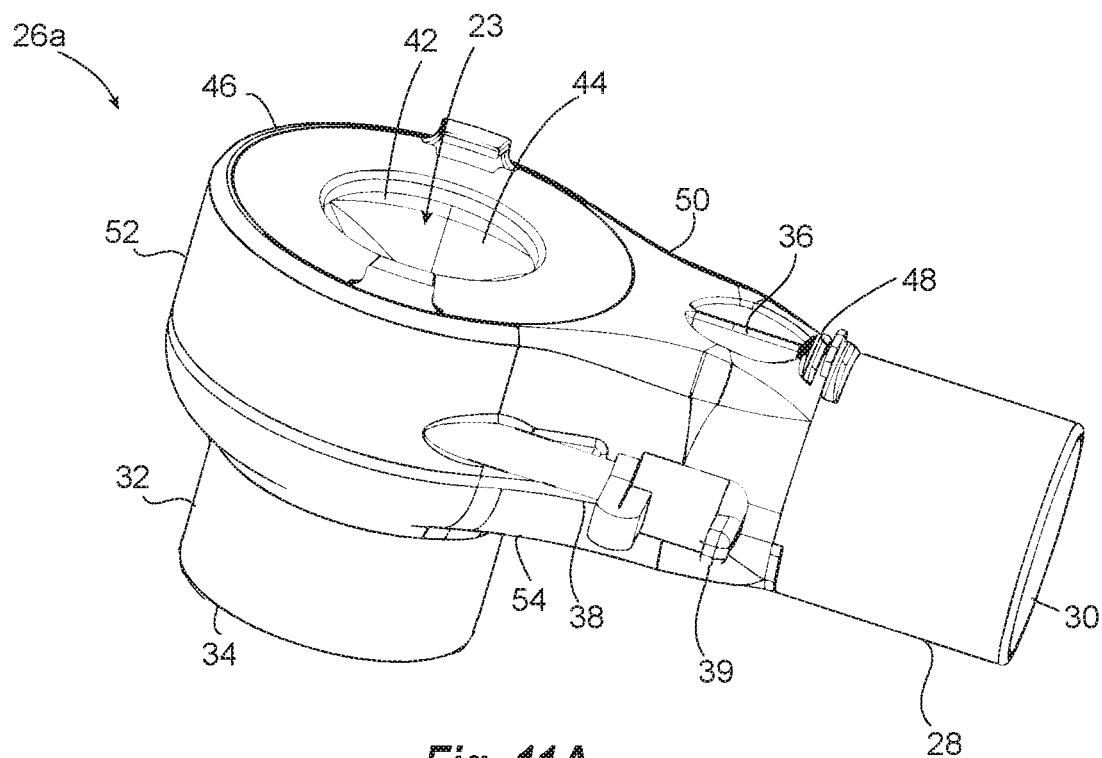
FIG. 11A is a perspective view of the elbow connector of FIG. 1A.
Figure 11B:
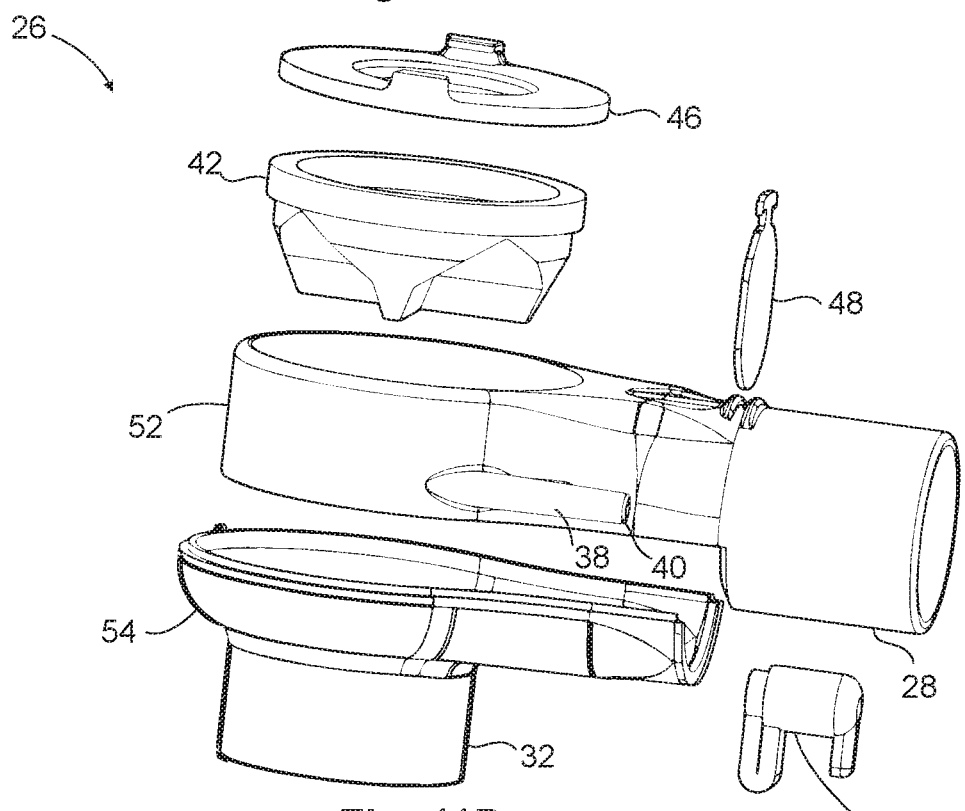
FIG. 11B is an exploded view of the elbow of FIG. 11A.
Figure 11C:
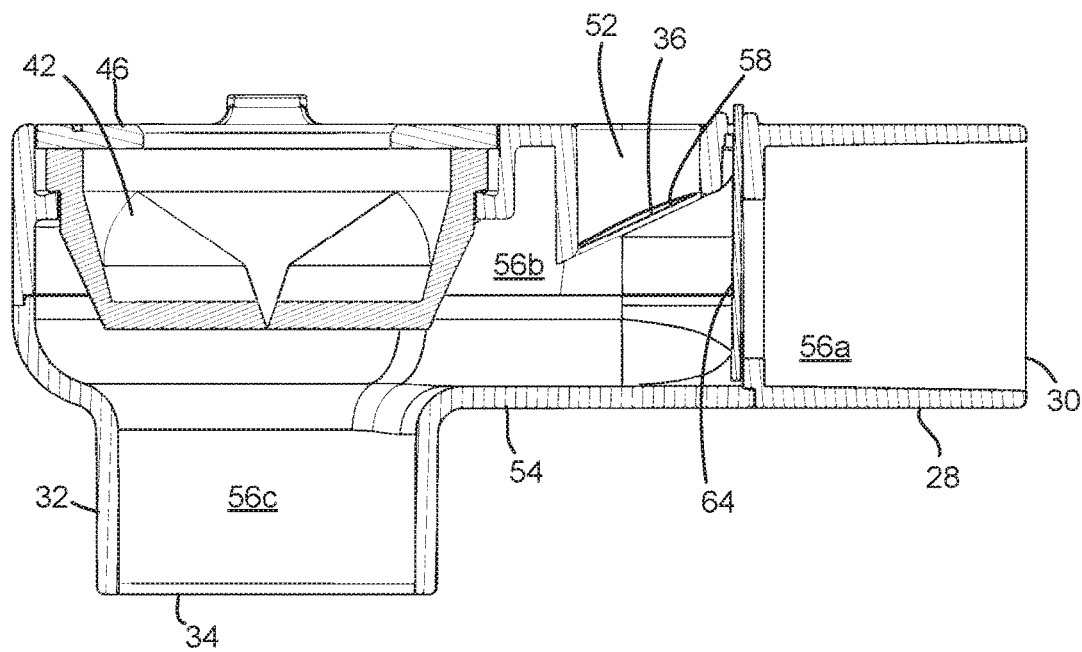
FIG. 11C is a cross section of the elbow of FIG. 11A.

FIGS. 11A-11C illustrate in more detail an elbow suitable for receiving a removable microphone module 100. Elbow 26 includes an elbow body 50 formed from upper housing 52 and lower housing 54. An access valve, such as cross-slit valve 42 is secured to upper housing 52 using a locking ring 46. Elbow 26 also includes an anti-asphyxiation valve that uses a flap 48 to open and close aperture 36. For purposes of this invention, unless otherwise stated or implied, the term "valve" by itself refers to the "access valve" in the access port 23.

With reference to FIG. 11C, elbow 26 is an air supply connector that includes an air-delivery conduit. The air supply conduit extends between inlet 30 and outlet 34 and includes internal regions 56a, 56b, and 56c. Valve 42 is in fluid communication with the air delivery conduit in region 56c. Valve 42 provides access to a wearer's mouth and nose through aperture 44 and region 56c of the conduit.

The air supply conduit provided by valve adapter 26 is configured to deliver pressurized air from a source of positive air pressure (e.g., ventilator unit 21) to the cavity of the ventilation mask 10. Air pressure in inlet 30 forces flap valve 48 to open to provide fluid communication between regions 56a and 56b. The air flow between region 56a and 56b forces flap 48 upward to close off aperture 36 by seating against seat 58. If air flow stops between regions 56a and 56b, flap 48 drops down to opening 64 to prevent air from flowing backwards through inlet 30 (i.e., from region 56a to 56b). Flap 48 prevents asphyxiation by allowing air to be breathed from the ambient (through aperture 36) if the supply of air from the ventilator is interrupted.

Elbow 26 includes a first press-fit connector 28 that serves to fluidly connect a positive pressure air supply hose (not shown) to inlet 30 of elbow 26. A second press-fit connector 32 serves to fluidly connect the outlet 34 of elbow 26 to an inlet in mask body 12. The press-fit connection may be configured to be sufficiently tight that when an appliance is positioned in the adapter (see FIG. 1B) and pulled out of valve 42, the press fit maintains the connection of the air supply connector to the mask. FIG. 1A illustrates a mask with a swivel connector 29 configured on the body of the mask 12. A press fit connector 32 is placed inside of the swivel connector 29 and is configured to be sufficiently tight to deliver air to the mask. The swivel connector has textured finger grips 19 that are used to press on the swivel or rotate the elbow 26.

Elbow 26 preferably swivels relative to mask body 12 such that a hose connected to an elbow 26 can be redirected without torqueing the mask. Any swivel mechanism can be used. The swivel mechanism may be incorporated into a mask body, elbow, or the connection there between.

Connections other than press-fit may be used to connect an elbow 26 to a mask or ventilation system, including non-removable connections, screw fit with screw threads, snap connection, slide in connection with securing ridges, clips, and quick release connections.

FIG. 14 illustrates an embodiment wherein an elbow 526 is configured to form a swivel connection with a mask. A swivel connection portion 300 is shaped to fit in an opening of a PPV mask. The swivel connector 300 is also configured with a sealing rim 304 that will seal with the edges of an opening on the mask. The elbow includes clip connectors 302 that snap into a ridge or mount on the body of the mask to keep the elbow securely fit and sealed on the access port. Release tabs 306 are attached to the clip connector that flex when pressed inward to release the elbow form the mask.

With reference again to FIGS. 11A-11C, elbow 26 may also include a pressure port 40 on stem 38. Pressure port 40 includes a small opening in fluid communication with region 56b that is used to monitor pressure changes in elbow 26. Changes in pressure can be used to detect when the wearer of the mask is inhaling or exhaling. Bi-level pressure ventilators can use the pressure port 40 to provide lower pressure during exhalation and increased pressure during inhalation. Pressure port 40 is not required to be associated with elbow 26, but rather can be placed in mask body 12, tubing between the ventilator and mask, or combinations of these. Pressure port 40 is can be covered with a cap 39 to plug and stop flow when detection is not necessary.

Elbow 26 has an access port 23 with aperture 44 and a valve 42 positioned within the port. Valve 42 may be a seal-sealing valve that uses pressure from the ventilator to close the valve when the access port is clear of an appliance or adapter. The access valve has an open diameter sufficient to perform oral care or insert appliance therethrough with reduced leaking as compared to an access port without the valve and having the same maximum diameter opening. The diameter of the opening in the self-sealing valve (in the fully open position) can be at least 5, 10, 15, or 20 mm (~0.2, 0.04, 0.06, 0.08 in) and/or less than 50, 40, 30, 25, or 20 mm (~2, 0.16, 0.12, 0.1, 0.08 in) and/or within a range of the foregoing (in the height and/or width of the opening based on a cross section of the opening). These diameters of opening can be achieved with a valve that will be self-sealing under pressures of at least 4, 5, 8, or 10 cm $H_2O$ and/or less than 30, 25, 20, 15 cm $H_2O$, or within a range of any of the foregoing endpoints.

In some embodiments, the opening in access valve 42 is provided by one or more slits. The length of the slit may provide the maximum open width. In some embodiments, the valve includes a plurality of slits. In some embodiments, the valve can include 2 slits and the slits may form a cross-slit.

Figures 12A, 12B:
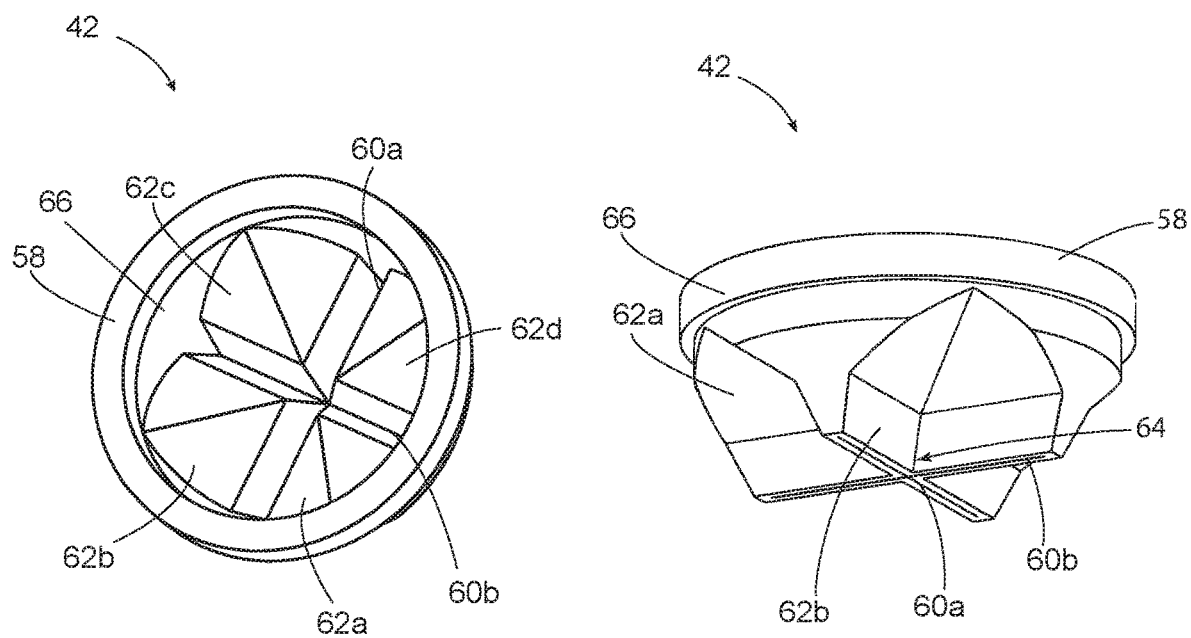
FIG. 12A is top perspective view of the self-sealing valve of the elbow of FIG. 11A.
FIG. 12B is a bottom perspective view of the valve of FIG. 12A.

To facilitate self-sealing under pressure, access valve 42 may have inward sloping walls or concavity that the pressure pushes against. Valve 42 may be a duck bill valve or a dome shaped valve. FIGS. 12A and 12B illustrate a duckbill valve with a cross-slit. Valve 42 has a rim 58, support wall 66, and a plurality of leaflets 62a-d. As seen in the top view of FIG. 12A the leaflets are each concave relative to the ventilator pressure side of the valve and form fenestrations at slits 60a and 60b. The leaflets 62 are configured to be pushed open by an appliance or appliance adapter from an outside side of the valve and pushed together by pressure from the inside side of the valve. The duck bill valve is shown with 4 leaflets, but may have a single leaflet (i.e., seals against a rigid wall) but more preferably has at least 2, 3, 4, or more leaflets. As shown in FIG. 12B the concavity of leaflets 62 have a geometry that meets near the center of the cross slit. For example, the concavity of leaflet 62b meets near point 64. When an appliance or adapter is inserted the leaflet 62*b* is forced out and point 64 moves away from the center cross, thereby opening the valve. Valve 42 can be made from an elastomeric material with shape memory such that upon removing the appliance or adapter, the device recovers at least a portion of its concavity such that the pressure can seal the leaflets.

Where a dome valve is used, the dome may have a tapered thickness that is thin at a center opening and tapers to a greater thickness towards the edges. The taper may include a change of thickness greater than 1.2, 1.5, or 2 times the thickness at a lateral edge of a fenestration/slits as compared to a center edge of a fenestration. The taper may allow the valve to open more easily at the center.

In a preferred embodiment, the valve reverts itself if it becomes inverted (i.e., self-reverting). For purposes of this invention, a self-reverting valve has a material and configuration that causes the valve to return to its self-sealing position when inverted (e.g., an elastomeric material with shape memory). Thus, if an instrument is pulled out of the valve and a leaflet or other component is inverted, the self-reverting valve returns to its self-sealing position once the force is removed. Although not required, the valve may be concave and/or made of a silicone material (or similar polymers, elastomers, isoprene, Nitrile rubber, Butyl rubber, or silicone like material) to facilitate self-reverting. In one embodiment, the valve includes a layer of material at its center that is less than 5, 4, 3, or 2 mm thick. The rim 58 of valve 42 also contributes to the self-reverting feature. The height of the rim above the leaflets and the material extending laterally provide rigidity to the wall buckling when valve 42 is inverted and the material between rim 58 and the leaflets stretching force the leaflets back to their correct position.

The access valve 42 and/or combination of one or more of the access valve 42, anti-asphyxiation valve 40, and mask 12 may be configured to have a leak rate less than 70, 50, 40, 30, or 25 liters per minute ("lpm") and/or greater than 2, 5, 7, or 10 lpm and/or within a range of the foregoing when the mask is under an air pressure of at least 5, 10, 15, cm H$_2$O and/or less than 25, 20, or 15 cm H$_2$O or within a range of the foregoing. For purposes of this invention, the leak rate is measured at a pressure of 5 cmH2O when measured in accordance with ISO standard 17510 (2015).

In some embodiments, the valve may include a biocompatible lubricant to facilitate insertion of appliances or appliance adapter through the valve. The access valve and/or lubricant may also include an anti-microbial agent (e.g., chlorhexidine). In some embodiments, the valve adapter may have a dust cap that covers the opening to valve 42 the valve is not in use.

Figure 7:
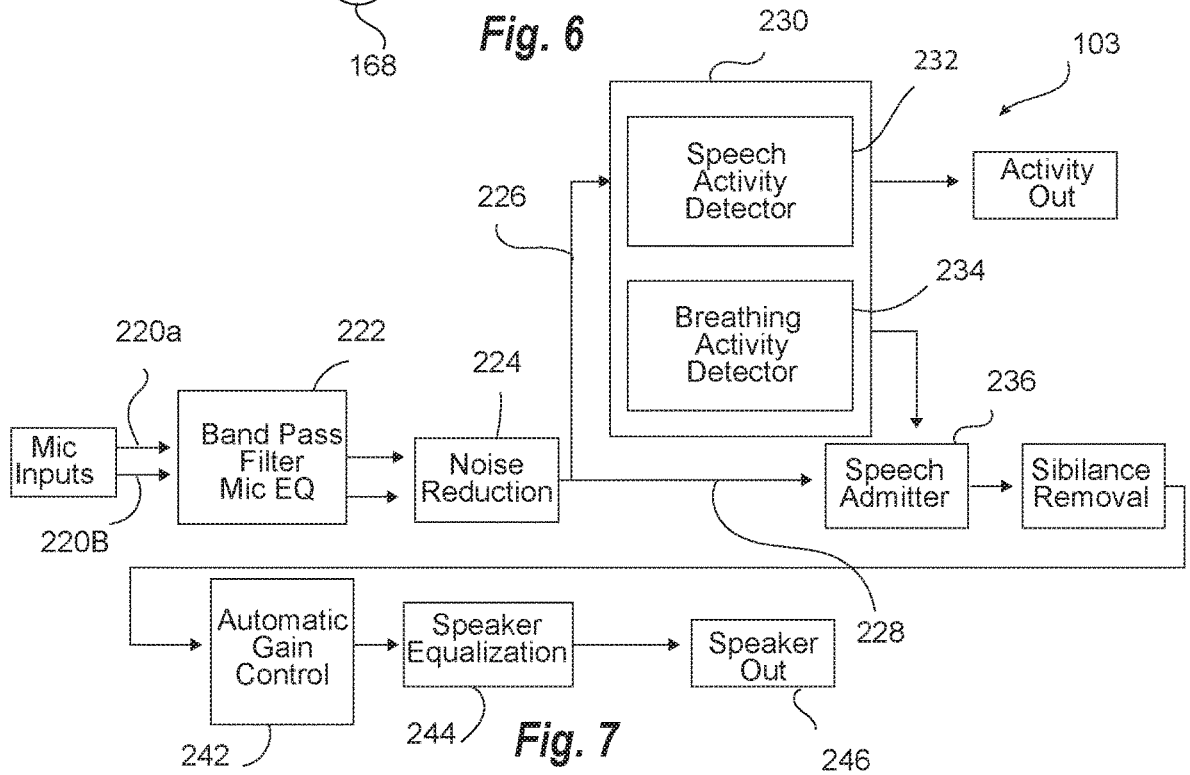
FIG. 7 is a diagram of digital signal processing for patient activity detection in the DSP of FIG. 6.

FIG. 13A shows an alternative embodiment with an elbow 426 that does not include the access valve 42 of elbow 26 from FIG. 1A. Elbow 426 includes an aperture 44 configured to receive appliance adapters that will seal the aperture 44 when the adapter is attached and/or placed through the aperture 44 (see FIGS. 7A-C). Because access port 23 of elbow 426 does not have a valve that seals the port when not in use, elbow 426 includes a seal cap 49 that can be placed over or in aperture 44 to prevent air leakage and to maintain air pressure between the mask and the face.

FIG. 13B illustrates an alternative embodiment of a mask 10 having a shell 12*b* that incorporates the access port 23 into the shell 12*b* instead of the elbow connector. Shell 12*b* has an elbow connector 27 separate from access port 23. Elbow connector 27 supplies pressurized air to the mask and may have any features known in the art for elbow connectors used on PPV masks. Similar to mask 10 of FIG. 1A, valve 42 seals access port 23 using positive pressure in mask 10. Placing access port 23 in the mask separate from the elbow connector allows elbow 27 to be smaller than elbow 26 of FIG. 1A.

The access port in shell 12*b* may also be configured without a valve as shown in access port 423 of FIG. 13A. In addition, access ports 23 (with or without a valve) can be placed anywhere on shell 12*b* that allows direct external access to the mouth or nose of the patient (i.e., access to the mouth or nose through the mask). In some embodiments, a microphone module and/or microphone can be incorporated into a shell of the mask with the microphone elements positioned inside the mask. The microphone elements may be permanently positioned in the shell of the mask.

FIG. 13B also illustrates one embodiment showing a mask body 12*b* with a flexible portion 106 that is more flexible than the material of the adjacent portion of mask body 12*b*. The flexible portion 106 provides greater articulation and movement for appliance adapters placed through the access valve 42 as well as support and flexibility in maintaining a seal around the face created by the cushion 22. The flexible portion 106 of shell 12*b* can also be incorporated into mask body of the embodiments shown in FIGS. 1A and 13A. In an alternative embodiment, the swivel connector 29 of FIG. 1A or 13A can be configured to be more flexible than the body of the mask 12. Flexible elbow connectors are further described in U.S. Pat. No. 8,302,605 which is hereby incorporated herein by reference. In yet another embodiment, the access port may be an iris valve such as the valve described in US2003/047189 to Kumar, which is hereby incorporated by reference.

The present invention also includes methods for using any of the other appliances described herein.

Figure 15A:
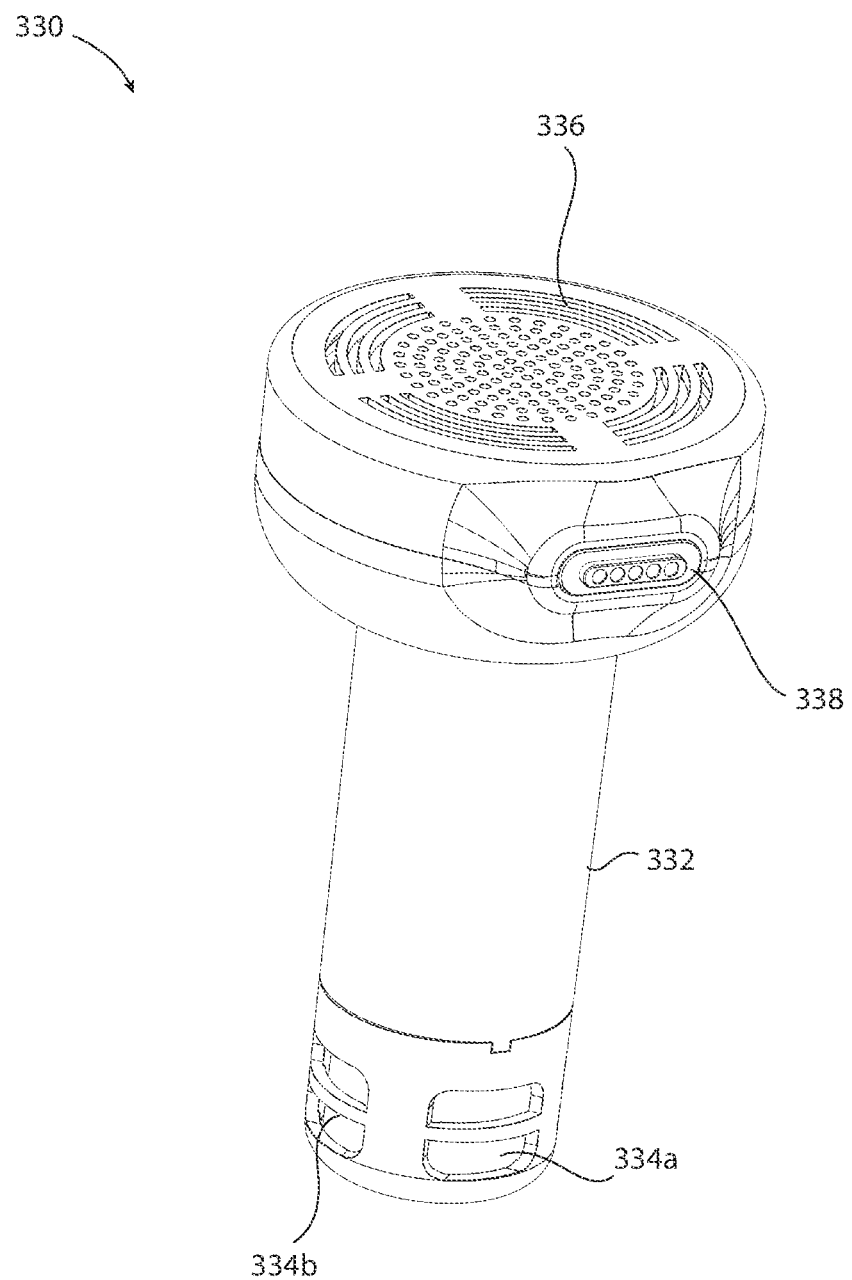
FIG. 15A illustrate a perspective view of a microphone module according to an alternative embodiment.
Figure 15B:
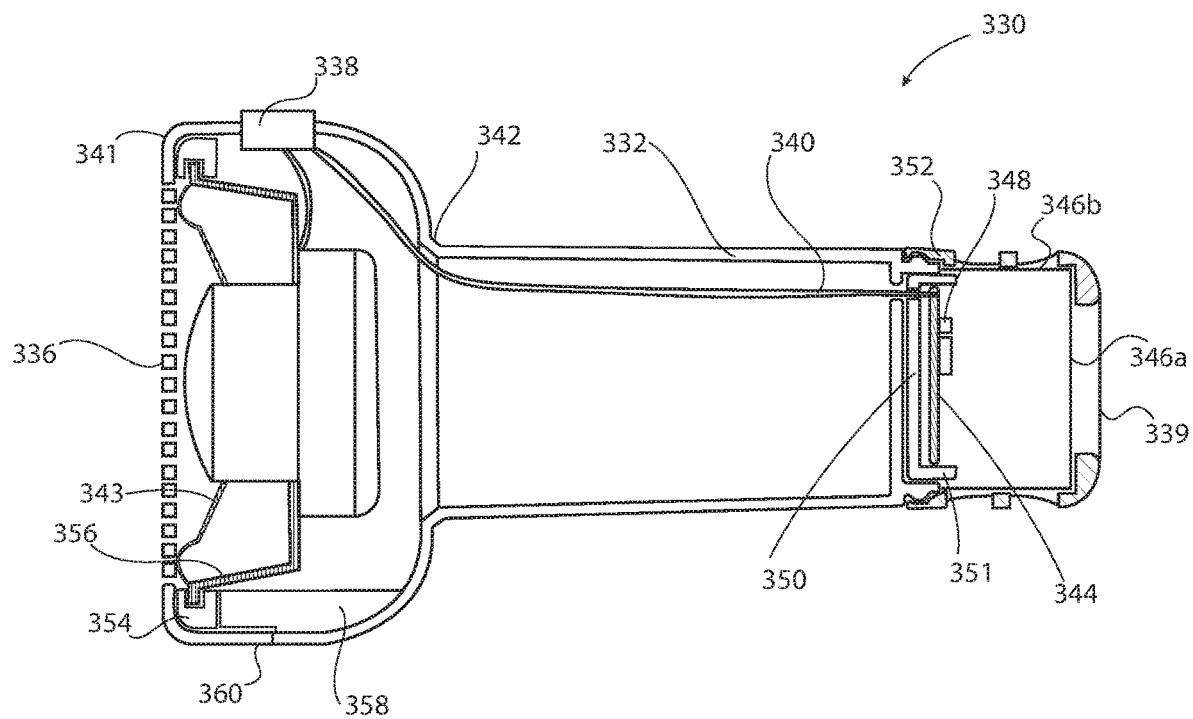
FIG. 15B is a cross section view of the microphone module of FIG. 15A with the back-cavity foam and attenuating foam removed and showing electrical wiring.
Figure 15C:
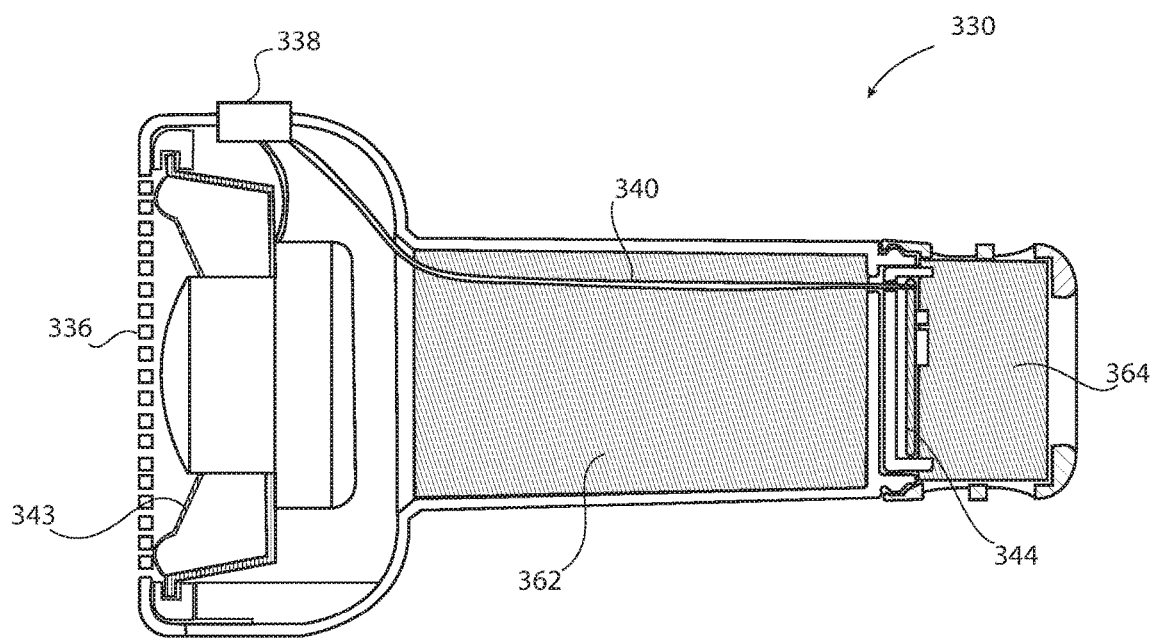
FIG. 15C is a cross section view of the microphone module of FIG. 15A showing the back-cavity foam and attenuating foam.

FIGS. 15A-15C describe an alternative embodiment of a microphone module 330 according to an alternative embodiment of the present invention. Microphone module has many of the same components as module 100. Module 336 has a housing 332 that defines an adapter configured to be inserted into an access port and form a seal with the access port. For example, structure 342 is configured to form a seal with an access port when module 330 is completely inserted.

Module 330 includes a plurality of openings 334 (e.g., 334*a* and 334*b*) that are protected by an acoustical mesh and allow vibrations to flow in of and/or out of the microphone compartment. The acoustical mesh may have a hydrophobic coating that inhibits penetration of water. FIG. 15B shows a cross section of microphone module 330. An end 339 of housing 332 is protected by acoustical mesh 346. End 339 is directed at the mouth of the patient when module 330 is positioned in an access port of the mask and mesh 346 allows sound from a patient's mouth to be directed directly at microphone element 348. Acoustical mesh 346*b* is on a lateral side and allows sound pressure entering end 339 to escape on a lateral side of the housing, which reduces eco or hollow effects in the microphone compartment.

Referring still to FIG. 15B, housing 332 has a joint 352 that allows the housing to snap together after electrical components are installed in the microphone cavity. A circuit board 344 is mounted within a vibration dampening gasket 350. Gasket 350 has a wall 351 that wraps up around the circuit board 344 to ensure that the board 344 does not directly contact housing 332. Circuit board 344 is electrically coupled to connector 338 (e.g., a magnetic connector with 3, 4, or 5 pins or more) through wiring 340. Wiring 340 passes through the speaker compartment inside housing 332 and into the microphone compartment. The wires pass through a slit in gasket 350. Slit 350 can compress around wires 340 to form a seal that prevents air from the speaker compartment to enter the microphone compartment.

Speaker 343 is housed within housing 332 and can be supported by a plurality of braces on a perimeter thereof (e.g., brace 358). A gasket such as C shaped gasket 354 can isolate speaker 343 from housing 332. Gasket 354 can be made of any vibration dampening material (e.g., silicone).

FIG. 15C shows the microphone compartment of module 330 filled with an attenuator (e.g., a dense foam). FIG. 15C also shows the back cavity of speaker 343 filled with foam 362 to give the back cavity a larger apparent volume.

Applicants U.S. Provisional Patent Application No. 62/568,314, filed Oct. 4, 2017 and 62/612,303, filed Dec. 29, 2017, and Applicant's PCT application No. PCT/US2016/039117, filed Jun. 23, 2016, and PCT/US2017/060480, Filed Nov. 7, 2017 are each hereby incorporated herein by reference in their entirety.

The present invention can be incorporated into various masks and/or adapters using a variety of materials. Examples of positive air pressure masks that can be adapted to include a valve according to one embodiment of the invention are illustrated in U.S. Patent Application publications US2009/0194111 to Fu et al and US2010/0116276 to Bayasi. The method of the present invention are not limited to the novel masks and mask systems described herein. For example, the methods can be carried out using the mask of U.S. Pat. No. 6,792,943 or 8,365,734 to Lehman. The foregoing patents and applications are incorporated herein by reference for their teachings of masks and components that can be used in combination with the features of the present invention and their use for carrying out the methods described herein.

We claim:

1. A positive pressure ventilation (PPV) patient microphone module, comprising:
    a housing defining an adapter configured to removably attach to and form a PPV seal with an access port of a PPV mask when attached thereto, the housing defining a speaker compartment and a microphone compartment;
    a loudspeaker positioned in the speaker compartment and forming a back cavity behind the speaker;
    a microphone element positioned in the microphone compartment and configured to receive voice signals, wherein the microphone element is mounted on a microphone circuit board disposed in the microphone compartment, and wherein a vibration dampening material is disposed between a wall of the housing and the microphone circuit board, wherein the microphone compartment is sealed off from the speaker compartment; and
    one or more electrical connectors electrically coupled to the microphone element and the loudspeaker, the one or more electrical connectors configured to transmit a microphone signal from the microphone element toward a controller module that is wired to and separate from the microphone module and the PPV mask, the microphone module also configured to receive an amplified signal from the controller module to drive the loudspeaker within the microphone module.

2. The patient microphone module of claim 1, wherein the adapter slidably attaches to the access port of the PPV mask.

3. The patient microphone module of claim 1, wherein at least a portion of the housing defines the back cavity and the back cavity is configured to extend through the access port and into the PPV mask.

4. The patient microphone module of claim 1, further comprising a female connector disposed in the housing and configured to transmit the microphone signal toward the controller module.

5. The patient microphone module of claim 4, wherein the female connector is magnetic and configured to couple to a male magnetic connector of an electrical cable that is also configured to connect to the controller module.

6. The patient microphone module of claim 1, wherein wiring electrically couples the one or more electrical connectors to the microphone element, the wiring passing through the speaker compartment into the microphone compartment, wherein the seal is formed around the wiring.

7. The patient microphone module of claim 1, wherein the loudspeaker has a diameter in a range between 15 mm to 60 mm.

8. The patient microphone module of claim 1, wherein the microphone compartment includes a sound attenuator.

9. The patient microphone module of claim 1, wherein the controller module further comprises:
    a microcontroller;
    an aerosol control circuit configured to generate a nebulizer signal for operating a vibrating mesh nebulizer;
    a microphone control circuit configured to receive the microphone signal and output a speaker signal;
    a power amplifier configured to amplify the nebulizer signal and the microphone signal, independently;
    a housing that encloses the microcontroller, power amplifier, aerosol control circuit, and microphone control circuit; and
    wherein the one or more electrical connectors comprise one or more cables or cable connectors configured to:
    (i) transmit the amplified nebulizer signal toward a nebulizer electrically wired to and separate from the controller module;
    (ii) receive the microphone signal from the one or more electrical connectors of the microphone module that is electrically wired to and separate from the controller module, the one or more cables or cable connectors of the controller module also configured to transmit the amplified microphone signal to the microphone module to drive a loudspeaker within the microphone module.

10. The patient microphone module of claim 9, wherein the controller module further comprises a control panel for receiving input from a user, the control panel providing control of speaker loudness.

11. The patient microphone module of claim 10, wherein the control panel provides user selection for finite nebulization and continuous nebulization.

12. The patient microphone module of claim 10, wherein the controller module further comprises an attachment configured to mount the controller module to a ventilator unit.

13. The patient microphone module of claim 12, wherein the attachment includes a screw mount positioned in the housing of the controller module.

14. The patient microphone module of claim 12, wherein the attachment includes a clamp configured to attach to a rail of a ventilator.

15. The patient microphone module of claim 1, wherein at least a portion of the speaker compartment forms a tubular structure configured to pass through the access port of the PPV mask and occupy space on an inside of the PPV mask when the microphone module is attached thereto.

16. The patient microphone module of claim 15, wherein the back cavity has a volume of at least 10 ml.

17. The patient microphone module of claim 16, wherein the back cavity has a foam disposed therein.

18. A non-invasive positive pressure ventilator system, comprising:

a positive pressure ventilation (PPV) mask including an access port;

a pressure generating unit configured to deliver positive air pressure through ventilator tubing to the PPV mask and to a person undergoing positive pressure ventilation;

a ventilator control unit configured to control the pressure generating unit; and a controller module configured to control generation of an aerosol and amplify a patient's voice, comprising:

a microcontroller;

an aerosol control circuit configured to generate an aerosol generator signal for operating a vibrating mesh nebulizer;

a microphone control circuit configured to receive a microphone signal and output a speaker signal;

a power amplifier configured to amplify the aerosol generator signal and the microphone signal, independently; and one or more cables or cable connectors configured to:

(i) transmit the amplified aerosol generator signal to a nebulizer module electrically wired to and separate from the controller module;

(ii) receive a microphone signal from a microphone module that is electrically wired to and separate from the controller module, the one or more cables or cable connectors of the controller module also configured to transmit the amplified microphone signal to the microphone module to drive a loudspeaker within the microphone module, wherein the nebulizer module and the microphone module are configured to removably attach to and form a PPV seal with the access port of the PPV mask when attached thereto, and wherein the nebulizer module and the microphone module are interchangeable with each other.

19. The non-invasive positive pressure ventilator system as in claim 18, wherein the microphone module further includes:

a housing defining an adapter configured to removably attach to and form a PPV seal with the access port of the PPV mask when attached thereto, the housing defining a speaker compartment and a microphone compartment;

a loudspeaker positioned in the speaker compartment and forming a back cavity behind the speaker;

a microphone element positioned in the microphone compartment and configured to receive voice signals, wherein the microphone compartment is sealed off from the speaker compartment.

20. The non-invasive positive pressure ventilator system as in claim 19, wherein the nebulizer module further includes:

a housing defining an adapter configured to removably attach to and form a PPV seal with the access port of the PPV mask when attached thereto, the housing defining a fluid reservoir for receiving a medicament;

a vibrating mesh positioned in the housing and configured to aerosolize medicament in the reservoir.

* * * * *